United States Patent

Mizushima et al.

[11] Patent Number: 5,599,483
[45] Date of Patent: Feb. 4, 1997

[54] N-ALKYLCARBAMYLALKANOL SULFATE OR SALT THEREOF, PROCESS FOR PRODUCING THE SAME AND DETERGENT COMPOSITION CONTAINING THE SAME

[75] Inventors: Hiromoto Mizushima; Masakatsu Takahashi; Akira Yamamuro, all of Wakayama; Takashi Matsuo, Chiba; Kazuyuki Yahagi, Tokyo, all of Japan

[73] Assignee: Kao Corporation, Tokyo, Japan

[21] Appl. No.: 540,977

[22] Filed: Oct. 11, 1995

Related U.S. Application Data

[63] Continuation-in-part of Ser. No. 511,100, Aug. 4, 1995, abandoned, which is a continuation of Ser. No. 230,242, Apr. 20, 1994, abandoned.

[30] Foreign Application Priority Data

Apr. 23, 1993 [JP] Japan ......................... 5-97848
Oct. 11, 1994 [JP] Japan ......................... 6-245178

[51] Int. Cl.$^6$ .................. C11D 1/18; C07C 305/00
[52] U.S. Cl. .................... 510/119; 510/126; 510/127; 510/130; 510/494; 510/495; 510/501; 510/123; 510/131; 510/159; 558/30; 546/347; 134/42
[58] Field of Search ................... 252/541, 544, 252/545, 549, 550, 551; 558/30; 546/347; 134/42

[56] References Cited

U.S. PATENT DOCUMENTS 2,120,512  6/1938  Rosenhauer ............... 260/124
2,255,082  9/1941  Orthner et al. ............ 260/458
2,632,766  3/1953  Benneville ................ 558/30

FOREIGN PATENT DOCUMENTS 0621265  10/1994  European Pat. Off. .
499022   1/1929   United Kingdom .
499022   2/1939   United Kingdom .

Primary Examiner—Paul Lieberman
Assistant Examiner—Caroline L. Dusheck
Attorney, Agent, or Firm—Birch, Stewart, Kolasch & Birch, LLP

[57] ABSTRACT

A N-alkylcarbamylalkanol sulfate or a salt thereof represented by the following general formula (1-1), a process for producing the same, and a detergent composition containing the same, which is useful as a detergent for hair, body or tableware and has not only excellent foaming power and detergency but also high safety:

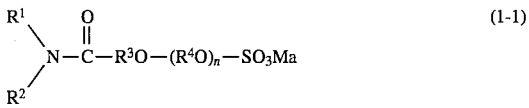

wherein $R^1$ represents a linear or branched alkyl or alkenyl group having 6 to 22 carbon atoms; $R^2$ represents an alkyl or alkenyl group having 1 to 22 carbon atoms or a hydrogen atom: $R^3$ represents a linear or branched alkylene group having 1 to 5 carbon atoms; $R^4O$ represents an oxyalkylene group having 2 or 3 carbon atoms; Ma represents a hydrogen atom, an alkali metal atom, an ammonium group, etc.; and n represents a number between 0 and 20.

20 Claims, No Drawings

N-ALKYLCARBAMYLALKANOL SULFATE OR SALT THEREOF, PROCESS FOR PRODUCING THE SAME AND DETERGENT COMPOSITION CONTAINING THE SAME

The present invention is a continuation-in-part of U.S. Ser. No. 08/511,100 filed on Aug. 4, 1995, now abandoned, which is a continuation application of U.S. Ser. No. 08/230,242, filed Apr. 20, 1994, now abandoned, the entire contents of which are incorporated herein by reference.

BACKGROUND OF THE INVENTION

1. Field of the Invention

The present invention relates to an N-alkylcarbamylalkanol sulfate and a salt thereof, which has excellent foaming power and detergency while being low in irritancy to the skin, so as to be widely useful as detergents for hair, skin, tableware, etc. The present invention also relates to a process for producing an N-alkyl-carbamylalkanol sulfate and a salt thereof and a detergent composition containing the same.

2. Description of the Related Art

In recent years, it is demanded that the surfactant used as a detergent have excellent surface activation capability and other properties, such as biodegradability and safety to the skin and eyes.

Surfactants satisfying the above demand include an acylated amino acid surfactant, an imidazoline surfactant and a saccharide surfactant such as an alkyl glycoside, which are widely used. However, these surfactants are generally poor in detergency and foaming power, which are especially important in a detergent. Therefore, their sole use as an ingredient in a shampoo or the like is uncommon, and they are generally used in combination with conventional anionic surfactants, such as an alkyl sulfate and an alkyl ether sulfate.

On the other hand, a sulfate of a monoethanolamide of a fatty acid and an isethionic ester are surfactants that are excellent in both safety and foaming power. However, these surfactants are unstable in solution.

Therefore, the development of a detergent having not only excellent foaming power and detergency, but also high safety and stability is strongly demanded in the art.

DISCLOSURE OF THE INVENTION

SUMMARY OF THE INVENTION

In view of the above situation, the present inventors have made extensive studies to develop a surfactant having not only excellent foaming power and detergency, but also high safety so as to be useful as a detergent for hair, body, tableware, etc. As a result, they have found that an N-alkylcarbamylalkanol sulfate having an amide group derived from a primary or secondary amine of a long chain and a sulfate group ($-OSO_3^-$), and a salt thereof are surfactants satisfying the above demand. Based on this finding, the present invention has been completed.

Thus, the present invention provides a N-alkylcarbamylalkanol sulfate or a salt thereof represented by the general formulae (1-1) or (1-2), a process for producing the same, and a detergent composition comprising the same, which has not only excellent foaming power and detergency but also high safety.

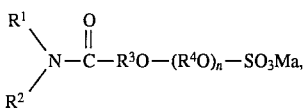

and

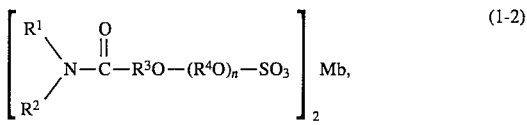

wherein $R^1$ represents a linear or branched alkyl or alkenyl group having 6 to 22 carbon atoms; $R^2$ represents a $C_1$–$C_{22}$ alkyl group, a $C_2$–$C_{22}$ alkenyl group or a hydrogen atom: $R^3$ represents a linear or branched alkylene group having 1 to 5 carbon atoms; $R^4O$ represents an oxyalkylene group having 2 or 3 carbon atoms; n represents an average addition mole number of the oxyalkylene group and is a number between 0 and 20, and wherein each $R^4O$ group may be the same or different from one another; Ma represents a hydrogen atom, an alkali metal atom, an ammonium group, an alkanolammonium group having 2 to 9 carbon atoms in total, an alkylammonium group having 1 to 22 carbon atoms in total, an alkenylammonium group having 2 to 22 carbon atoms in total, a $C_1$–$C_{18}$ alkyl- or $C_2$–$C_{18}$ alkenyl-substituted pyridinium group or a group consisting of a basic amino acid and a hydrogen atom; and Mb represents an alkaline earth metal atom).

Preferable N-alkylcarbamylalkanol sulfates and salts thereof according to the present invention include those belonging to the following groups A to E.

A. Salts of N-alkylcarbamylalkanol sulfates represented by the above general formula (1-1), wherein $R^1$ represents a linear or branched alkyl group having 6 to 22 carbon atoms; $R^2$ represents a hydrogen atom or a methyl group, preferably a hydrogen atom; $R^3$ represents a linear or branched alkylene group having 1 to 5 carbon atoms, preferably 2 to 5 carbon atoms; $R^4O$ represents an oxyethylene group or an oxypropylene group; n is a number between 0 and 10; and Ma represents an ammonium group, sodium, potassium or an alkanolammonium group having 2 to 9 carbon atoms in total.

B. Salts of N-alkylcarbamylalkanol sulfates represented by the above general formula (1-1), wherein $R^1$ represents a linear alkyl group having 8 to 18 carbon atoms; $R^2$ represents a hydrogen atom or a methyl group; $R^3$ represents a linear alkylene group having 1 to 5 carbon atoms; n is 0; and Ma represents an ammonium group, sodium or a triethanolammonium group.

C. Salts of N-alkylcarbamylalkanol sulfates represented by the above general formula (1-1), wherein $R^1$ represents a linear alkyl group having 8 to 18 carbon atoms; $R^2$ represents a hydrogen atom; $R^3$ represents a linear or branched alkylene group having 3 to 5 carbon atoms; n is 0; and Ma represents an ammonium group, sodium or a triethanolammonium group.

D. Salts of N-alkylcarbamylalkanol sulfates represented by the above general formula (1-1), wherein $R^1$ represents a linear alkyl group having 8 to 18 carbon atoms; $R^2$ represents a hydrogen atom; $R^3$ represents a methylene group, a pentamethylene group or a 2-methylbutylene group, preferably a 2-methylbutylene group; n is 0; and Ma represents an ammonium group, sodium or a triethanolammonium group.

E. Salts of N-alkylcarbamylalkanol sulfates represented by the above general formula (1-1), wherein $R^1$ represents a linear alkyl group having 8 to 18 carbon atoms; $R^2$ represents a hydrogen atom; $R^3$ represents a methylene group; n is 0; and Ma represents an ammonium group, sodium or a triethanolammonium group.

In other words, the N-alkylcarbamylalkanol sulfate and salts thereof according to the present invention is an N-alkylamidoalkanol sulfate or a salt thereof represented by the following general formula (I):

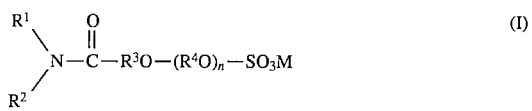

wherein $R^1$ represents a linear or branched alkyl group or alkenyl group having 6 to 22 carbon atoms; $R^2$ represents an alkyl or alkenyl group having 1 to 22 carbon atoms or a hydrogen atom; $R^3$ represents a linear or branched alkylene group having 1 to 5 carbon atoms; $R^4O$ represents an oxyalkylene group having 2 to 3 carbon atoms; n is an arbitrary number between 0 and 20, provided that n $R^4Os$ may be identical or different; and M represents a hydrogen atom, an alkali metal, an alkaline earth metal, ammonium, an alkanolammonium having 2 to 9 carbon atoms in total, an alkylammonium or alkenylammonium having 1 to 22 carbon atoms in total, an alkyl or alkenyl (having 1 to 18 carbon atoms) substituted pyridinium or a basic amino acid.

The present invention is also directed to a compound represented by the general formula (1-3):

(wherein $R^1$ stands for a linear or branched alkyl or alkenyl group having 8 to 18 carbon atoms) and detergent compositions containing the same.

In formula 1-3 it is preferable that $R^1$ is a linear or branched alkyl or alkenyl group having 10 to 14 carbon atoms, in particular a dodecyl group.

The detergent composition containing (1-3) above may further comprise a compound of the below described formula (1-4), preferably wherein M of the general formula (1-4) is sodium, ammonium or triethanolammonium.

(wherein $R^1$ stands for the same meaning as defined above; and M stands for an alkali metal except for potassium, an alkaline earth metal, ammonium, an alkanolammonium, an alkylammonium, an alkenylammonium, an alkyl- or alkenyl-substituted pyridinium, or a basic amino acid).

In addition, the invention provides a method for cleansing the skin or hair with the compound as defined above; use of the compound as defined above for cleansing skin or hair; and a method for manifesting a pearly luster to a detergent composition by using the compound (1-3) as defined above.

In the general formula (1-3), $R^1$ stands for a linear or branched alkyl or alkenyl group having 8 to 18 carbon atoms, specific examples of which include an octyl group, a decyl group, a dodecyl group, a tetradecyl group, a hexadecyl group, an octadecyl group, an isostearyl group, and an oleyl group. Among them, those having 10 to 14 carbon atoms are preferred, and a dodecyl group is especially preferred because it provides high foaming properties and detergency as well as easily provides an appearance of pearly luster at ordinary temperature.

Although a detergent composition of the present invention comprising the compound represented by the general formula (1-3) can assume a pearly luster, the compound represented by the general formula (1-3) sometimes has a high temperature for manifesting a pearly luster. Thus, a compound represented by the following general formula (1-4) is preferably blended in the detergent composition comprising the compound of general formula (1-3) since the temperature for manifesting a pearly luster can be controlled without any adverse effects on the detergency and foaming properties of the composition:

(wherein $R^1$ stands for the same meaning as defined above; and M stands for an alkali metal except for potassium, an alkaline earth metal, ammonium, an alkanolammonium, an alkylammonium, an alkenylammonium, an alkyl- or alkenyl-substituted pyridinium, or a basic amino acid).

In the general formula (1-4), M may be selected from the group consisting of alkali metals except for potassium; alkaline earth metals; ammonium; alkanolammoniums, preferably alkanolammoniums having 2 to 9 carbon atoms in total; alkylammoniums or alkenylammoniums having 1 to 22 carbon atoms in total; pyridinium substituted with alkyl or alkenyl having 1 to 18 carbon atoms in total; and basic amino acids. Among them, sodium, ammonium and triethanolammonium are especially preferred.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

First, the N-alkylcarbamylalkanol sulfates and salts thereof according to the present invention are described.

Although in the general formulae (1-1) and (1-2), $R^1$ represents a linear or branched alkyl group or alkenyl group having 6 to 22 carbon atoms, $R^1$ preferably represents a linear or branched alkyl group having 6 to 22 carbon atoms, and more preferably a linear alkyl group having 8 to 18 carbon atoms, from the viewpoint of foaming power of surfactants represented by these formulae. Examples of alkyl groups of $R^1$ include hexyl group, octyl group, decyl group, dodecyl group, tetradecyl group, hexadecyl group, octadecyl group, isostearyl group, eicosyl group and docosyl group, while examples of alkenyl groups of $R^1$ include octadecenyl group.

Although $R^2$ represents an alkyl or alkenyl group having 1 to 22 carbon atoms or a hydrogen atom, $R^2$ preferably represents a hydrogen atom or a methyl group, and more preferably a hydrogen atom, from the viewpoints of foaming power, safety and chemical stability of surfactants represented by the general formulae (1-1) or (1-2). Examples of alkyl groups of $R^2$ include a methyl group, an ethyl group, a propyl group, a butyl group and alkyl groups mentioned as examples of $R^1$, while examples of alkenyl groups of $R^1$ include octadecenyl group.

Although $R^3$ represents a linear or branched alkylene group having 1 to 5 carbon atoms, $R^3$ preferably represents a linear or branched alkylene group having 2 to 5 carbon atoms, and more preferably a linear or branched alkylene group having 3 to 5 carbon atoms. Specific examples of the alkylene groups include a methylene group, a pentamethylene group (pentylene group) and a 2-methylbutylene group. A methylene group is preferred from the viewpoints of foaming power and chemical stability of surfactants represented by the general formulae (1-1) or (1-2).

$R^4O$ represents an oxyalkylene group having 2 or 3 carbon atoms. That is, $R^4O$ represents —$CH_2CH_2O$—, —$CH_2CH_2CH_2O$— or —$CH_2CH(CH_3)O$—, and preferably —$CH_2CH_2O$— (oxyethylene group) or —$CH_2CH(CH_3)O$— (oxypropylene group). The oxyalkylene group may be only one oxyalkylene group or a mixture of at least two oxyalkylene groups.

n represents an average value of the number of oxyalkylene groups which are contained in a surfactant represented by the general formulae (1-1) or (1-2) (an average addition mole number of alkyleneoxide group). n is a number between 0 and 20, preferably between 0 and 10 and more preferably 0.

Ma in the general formula (1-1) represents a hydrogen atom, an alkali metal atom, an ammonium group, an alkanolammonium group having 2 to 9 carbon atoms in total, an alkylammonium group having 1 to 22 carbon atoms in total, an alkenylammonium group having 2 to 22 carbon atoms in total, a $C_1$–$C_{18}$ alkyl- or $C_2$–$C_{18}$ alkenyl-substituted pyridinium group or a group consisting of a basic amino acid and a hydrogen atom. From the viewpoint of foaming power of the surfactant, Ma preferably represents an ammonium group, sodium, potassium or an alkanolammonium group having 2 to 9 carbon atoms in total and still more preferably an ammonium group, sodium or a triethanolammonium group.

Mb in the general formula (1-2) represents an alkaline earth metal atom.

Suitable examples of salts of N-alkylcarbamylalkanol sulfate represented by the above general formulae (1-1) or (1-2) according to the present invention include:

$CH_3(CH_2)_{11}NHCOCH_2OSO_3NH_4$,
$CH_3(CH_2)_{11}NHCO(CH_2)_5OSO_3NH_4$,
$CH_3(CH_2)_9NHCOCH_2OSO_3NH_4$,
$CH_3(CH_2)_{11}N(CH_3)COCH_2OSO_3Na$,
$CH_3(CH_2)_{11}NHCOCH_2OSO_3Na$,
$CH_3(CH_2)_{11}NHCO(CH_2)_2OSO_3Na$,
$CH_3(CH_2)_{11}NHCO(CH_2)_3OSO_3Na$,
$CH_3(CH_2)_{11}NHCO(CH_2)_4OSO_3Na$,
$CH_3(CH_2)_{11}NHCO(CH_2)_5OSO_3Na$,
$CH_3(CH_2)_{11}NHCOCH_2CH(CH_3)CH_2CH_2OSO_3Na$,
$CH_3(CH_3)_{11}NHCOCH_2CH(CH_3)CH_2CH_2OSO_3K$,
$CH_3(CH_2)_{13}NHCO(CH_2)_3OSO_3Na$,
$CH_3(CH_2)_{13}NHCO(CH_2)_3OSO_3NH_4$,
$CH_3(CH_2)_{13}NHCO(CH_2)_4OSO_3NH_4$,
$CH_3(CH_2)_9NHCO(CH_2)_3OSO_3Na$,
$CH_3(CH_2)_9NHCO(CH_2)_3OSO_3HN(CH_2CH_2OH)_3$,
$CH_3(CH_2)_9NHCO(CH_2)_3OSO_3H_2N(CH_2CH_2OH)_2$,
$CH_3(CH_2)_9NHCO(CH_2)_3OSO_3H_3NCH_2CH_2OH$,
$CH_3(CH_2)_9NHCO(CH_2)_5OSO_3Na$,
$CH_3(CH_2)_7NHCO(CH_2)_4OSO_3Na$,
$CH_3(CH_2)_{11}N(CH_3)CO(CH_2)_3OSO_3Na$,
$CH_3(CH_2)_{13}N(CH_3)CO(CH_2)_4OSO_3Na$,
$CH_3(CH_2)_{11}NHCO(CH_2)_3OCH_2CH_2OSO_3Na$,
$CH_3(CH_2)_{11}NHCO(CH_2)_4OCH_2CH(CH_3)OSO_3Na$, and
$CH_3(CH_2)_9NHCO(CH_2)_4O(CH_2CH_2O)_5SO_3Na$.

Next, the process for producing the N-alkylcarbamylalkanol sulfate or the salt thereof according to the present invention is described.

The N-alkylcarbamylalkanol sulfate or the salt thereof represented by the general formulae (1-1) or (1-2) according to the present invention can be easily produced by conducting steps selected from A to D in an order selected from the group consisting of (1) A, B and C, (2) A and C, (3) D, B and C, and (4) D and C:

Step A

Reacting an aliphatic amine represented by the general formula (2):

(wherein $R^1$ and $R^2$ are defined above), with a cyclic lactone represented by the general formula (3):

(wherein $R^3$ is defined above), to thereby obtain an N-alkylcarbamylalkanol represented by the general formula (4):

(wherein $R^1$, $R^2$ and $R^3$ are defined above);

Step B

Reacting the N-alkylcarbamylalkanol represented by the above general formula (4) with an alkylene oxide in the presence of an alkali or acid catalyst to thereby obtain an N-alkylcarbamylalkanol represented by the general formula (5):

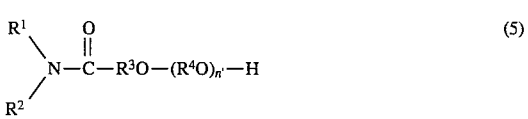

(wherein $R^1$, $R^2$, $R^1$ and $R^4O$ are defined above, and n' represents an average addition mole number of oxyalkylene group and is a number between 1 and 20);

Step C

Reacting the N-alkylcarbamylalkanol represented by the above general formulae (4) or (5) with a sulfating agent to thereby obtain an N-alkylcarbamylalkanol sulfate represented by the above general formula (1-1) (with the proviso that Ma is a hydrogen atom), and, if necessary, neutralizing the N-alkylcarbamylalkanol sulfate thus obtained with a basic compound to thereby obtain a salt of N-alkylcarbamylalkanol sulfate represented by the above general formulae (1-1) (with the proviso that Ma is not a hydrogen atom) or (1-2); and

Step D

Reacting the aliphatic amine represented by the above general formula (2) with an ω-hydroxycarboxylic acid or an ester thereof represented by the general formula (6): HO—R³CO₂R⁵ (6) (wherein R³ is defined above, and R⁵ represents a hydrogen atom or a linear or branched alkyl group having 1 to 4 carbon atoms) to thereby obtain an N-alkylcarbamylalkanol represented by the above general formula (4).

In other word, the the process for producing the N-alkylcarbamylalkanol sulfate, i.e., the N-alkylamidoalkanol sulfate, or the salt thereof according to the present invention comprises conducting the following steps A', B' and C'; A' and C'; D', B' and C'; or D' and C' in this order:

Step A'

Reacting an aliphatic amine represented by the general formula (2):

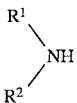 (2)

(wherein R¹ and R² are defined above), with a cyclic lactone represented by the general formula (3):

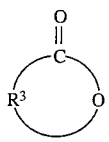 (3)

(wherein R³ is defined above), to thereby obtain an N-alkylamidoalkanol represented by the general formula (4):

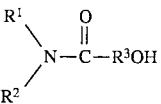 (4)

(wherein R¹, R² and R³ are defined above);

Step B'

Reacting the N-alkylamidoalkanol represented by the above general formula (4) with an alkylene oxide in the presence of an alkali or acid catalyst to thereby obtain an N-alkylamidoalkanol represented by the general formula (5):

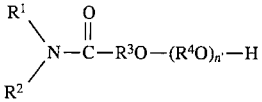 (5)

(wherein R¹, R², R³ and R⁴ are defined above, and n' represents a number of 1 to 20);

Step C'

Reacting the N-alkylamidoalkanol represented by the above general formulae (4) or (5) with a sulfating agent, and then neutralizing with a basic compound to thereby obtain a salt of N-alkylamidoalkanol sulfate represented by the above general formula (I); and

Step D'

Reacting the aliphatic amine represented by the above general formula (2) with an ω-hydroxycarboxylic acid or an ester thereof represented by the general formula (6): HO—R³CO₂R⁵ (6) (wherein R³ is as defined above, and R⁵ represents a hydrogen atom or a linear or branched alkyl group having 1 to 4 carbon atoms) to thereby obtain an N-alkylamidoalkanol represented by the above general formula (4).

Hereinbelow, each of the above steps will be described in greater detail.

Step A

This is a step in which an aliphatic amine represented by the above general formula (2) (hereinafter referred to simply as "aliphatic amine (2)") is reacted with a cyclic lactone represented by the above general formula (3) (hereinafter referred to simply as "cyclic lactone (3)") to thereby obtain an N-alkylcarbamylalkanol represented by the above general formula (4) (hereinafter referred to simply as "N-alkylcarbamylalkanol (4)").

The aliphatic amine (2) and cyclic lactone (3) as the starting compounds may be either those produced by known processes, or those commercially available. If desired, those purified by recrystallization, distillation or the like may be used.

Examples of aliphatic amines (2) include octylamine, decylamine, dodecylamine, tetradecylamine, hexadecylamine, octadecylamine, octylmethylamine, decylmethylamine, dodecylmethylamine, tetradecylmethylamine, hexadecylmethylamine and octadecylmethylamine. Among them, octylamine, decylamine, dodecylamine, tetradecylamine, hexadecylamine and octadecylamine are preferred, and octylamine, decylamine, dodecylamine and tetradecylamine are particularly preferred.

Examples of cyclic lactones (3) include β-propiolactone, γ-butyrolactone, δ-valerolactone, 2-methyl-δ-valerolactone, ε-caprolactone and 2-methyl-γ-butyrolactone. Among them, γ-butyrolactone, δ-valerolactone, 2-methyl-δ-valerolactone and ε-caprolactone are preferred, and 2-methyl-δ-valerolactone and ε-caprolactone are particularly preferred.

In this step, the N-alkylcarbamylalkanol (4) can be obtained by reacting an aliphatic amine (2) with a cyclic lactone (3) in an amount of 1 to 1.5 times by mol that of the aliphatic amine (2) in the absence of any solvent, or, if necessary, in a solvent such as toluene, xylene, dioxane and DMF, at an appropriate temperature between 0° and 180° C., preferably between 70° and 150° C., more preferably between 80° and 130° C. for 1 to 100 hrs, preferably 1 to 20 hrs.

When the reaction temperature exceeds 180° C., unfavorable side reactions, such as polymerization of the cyclic lactone (3), become marked.

The N-alkylcarbamylalkanol (4) obtained by this process may be used in the subsequent step as is. If desired, however, it may be purified by recrystallization from a solvent, such as hexane, methanol, ethanol, acetone and chloroform, to thereby obtain an N-alkylcarbamylalkanol having increased purity.

Step B

This is a step in which the N-alkylcarbamylalkanol (4) obtained in the steps A or D is reacted with an alkylene oxide in the presence of an alkali or acid catalyst to thereby obtain the N-alkylcarbamylalkanol represented by the above general formula (5) (hereinafter referred to simply as "N-alkylcarbamylalkanol (5)").

Examples of the alkali catalysts include alkali metal hydroxides, alkali metal carbonates, organic amines, metal oxides and alkoxides. Among them, NaOH and KOH are preferred.

Examples of the acid catalysts include Lewis acids and metal oxides, such as boron trifluoride ($BF_3$), tin tetrachloride ($SnCl_4$), antimony pentachloride ($SbCl_5$), magnesium oxide (MgO) and aluminum oxide ($Al_2O_3$). Among them, boron trifluoride and magnesium oxide are preferred.

Examples of the alkylene oxides include ethylene oxide and propylene oxide. Ethylene oxide is preferred.

In this step, the N-alkylcarbamylalkanol (5) can be obtained by reacting the N-alkylcarbamylalkanol (4) with a desired amount of an alkylene oxide in the presence of an acid or alkali catalyst in an amount of 0.5 to 5% by mol based on the molar number of the N-alkylcarbamylalkanol (4) as the starting compound at 120° to 180° C. for 1 to 10 hrs.

When the reaction temperature exceeds 180° C., various unfavorable by-products that cause discoloration or smell, such as aldehydes and peroxides, are yielded.

After the completion of the reaction, an alkali, such as NaOH and KOH, may be added to the reaction mixture in order to neutralize the acid catalyst, or an acid, such as phosphoric acid, acetic acid and lactic acid, may be added to the reaction mixture in order to neutralize the alkali catalyst. Alternatively or further, treatment of the reaction mixture with an acid or alkali adsorbent for purification may be effected to remove a salt.

Step C

This is a step in which the N-alkylcarbamylalkanol (4) or (5) is reacted with a sulfating agent to thereby obtain a N-alkylcarbamylalkanol sulfate represented by the above general formula (1-1) (with the proviso that Ma is a hydrogen atom), and then, if necessary, neutralizing the N-alkylcarbamylalkanol sulfate thus obtained with a basic compound to thereby obtain a salt of N-alkylcarbamylalkanol sulfate represented by the above general formulae (1-1) (with the proviso that Ma is not a hydrogen atom) or (1-2).

The N-alkylcarbamylalkanol sulfate or the salt thereof represented by the above general formula (1-1) is referred to simply as "N-alkylcarbamylalkanol sulfate or the salt thereof (1-1)" and the salt of N-alkylcarbamylalkanol sulfate represented by the above general formula (1-2) is referred to simply as "the salt of N-alkylcarbamylalkanol sulfate (1-2)", hereinafter.

Examples of the sulfating agents include chlorosulfonic acid, sulfuric anhydride, fuming sulfuric acid, concentrated sulfuric acid and sulfamic acid. From the viewpoint of reaction yield, chlorosulfonic acid, sulfuric anhydride and sulfamic acid are preferred.

Examples of the basic compound include a hydroxide, a carbonate or a bicarbonate of an alkali metal or alkaline earth metal, ammonia, an alkanolamine having 2 to 9 carbon atoms in total, an alkylamine having 1 to 22 carbon atoms in total, an alkenylamine having 2 to 22 carbon atoms in total, a $C_1$–$C_{18}$ alkyl- or $C_2$–$C_{18}$ alkenyl-substituted pyridine and a basic amino acid. Specific examples thereof include inorganic alkalis, such as sodium hydroxide, potassium hydroxide, lithium hydroxide, barium hydroxide, sodium hydrogencarbonate, sodium carbonate and potassium carbonate, ammonia, monoethanolamine, diethanolamine, triethanolamine, methylamine, dimethylamine, trimethylamine, ethylamine, diethylamine, triethylamine, decylamine, dodecylamine, tetradecylamine, hexadecylamine, octadecylamine and basic amino acids. Among them, ammonia, sodium hydroxide, potassium hydroxide, monoethanolamine, diethanolamine and triethanolamine are preferred. In this step, the above basic compounds may be used in the form of an aqueous or alcohol solution thereof to neutralize the sulfate. The degree of neutralization may be set at an arbitrary level.

In this step, a sulfating agent is used in an amount of 1 to 1.5 times by mol that of the N-alkylcarbamylalkanol (4) or the N-alkylcarbamylalkanol (5). The reaction is effected in a solvent, such as dichloromethane, chloroform, 1,2-dichloroethane, dimethylformamide, dimethyl sulfoxide and dioxane, in an amount of 0 to 10 times by volume that of the N-alkylcarbamylalkanol (4) or the N-alkylcarbamylalkanol (5) at −50° to 80° C., preferably −30° to 50° C. for 1 to 20 hrs. A sulfate (1-1) (with the proviso that Ma is a hydrogen atom) corresponding to the N-alkylcarbamylalkanol (4) or the N-alkylcarbamylalkanol (5) used can be obtained thereby.

The solvent to be used must be purified until there is scarcely any water or alcohol contained therein. The sulfation reaction can be conducted in the absence of any solvent. Without the solvent, however, the viscosity of the reaction mixture is extremely increased, so that countermeasures with respect to the equipment will be required.

Further, when the reaction temperature exceeds 80° C., unfavorable side reactions, such as cleavage of an amide group, would occur.

After the completion of the sulfation reaction, if desired, the solvent used in the sulfation reaction is distilled off. The distillation of the solvent can be conducted after the neutralization, which will be described hereinbelow.

Thereafter, the sulfate obtained by the above reaction is neutralized with a basic compound in an amount of 0.9 to 1.5 times by equivalent that of the N-alkylcarbamylalkanol (4) or the N-alkylcarbamylalkanol (5) in a solvent, such as water, ethanol and methanol, at −50° to 80° C. for 0.1 to 1 hr to thereby obtain a salt of N-alkylcarbamylalkanol sulfate (1-1) (with the proviso that Ma is not a hydrogen atom) or (1-2).

By-products, such as N-alkylcarbamylalkanols, lactones and amines, are present in the reaction mixture obtained by the above neutralization reaction. Depending on use, the reaction mixture can be employed as it is. If desired, however, the reaction mixture is purified by recrystallization, column chromatography, electrodialysis, solvent extraction, etc., to thereby obtain a product having increased purity.

Step D

This is a step in which the aliphatic amine (2) is reacted with an ω-hydroxycarboxylic acid or an ester thereof represented by the above general formula (6) (hereinafter referred to simply as "ω-hydroxycarboxylic acid or ester (6)"), preferably an ω-hydroxycarboxylic ester (6), to thereby obtain a N-alkylcarbamylalkanol (4).

Needless to say, this step includes a step in which the aliphatic amine (2) is reacted with an ω-hydroxycarboxylic acid represented by the general formula (6'): HO—$R^3CO_2H$ (6') (wherein $R^3$ is defined above) to thereby obtain a N-alkylcarbamylalkanol (4).

Examples of the ω-hydroxycarboxylic acids or esters (6) include lactic acid, glycolic acid (1-hydroxyacetic acid), 2-hydroxypropionic acid, 3-hydroxybutyric acid, 4-hydroxypentanoic acid, 4-hydroxy-3-methylpentanoic acid and 5-hydroxyhexanoic acid, and methyl, ethyl, propyl and butyl esters thereof. From the viewpoints of foaming power and chemical stability of the surfactant to be obtained by this production process, desired examples of ω-hydroxycarboxylic acids include 3-hydroxybutyric acid, 4-hydroxypentanoic acid, 4-hydroxy-3-methylpentanoic acid and 5-hydroxyhexanoic acid. From the viewpoints of foaming power and chemical stability of the surfactant to be obtained by this production process, desired examples of ω-hydroxycarboxylic acid esters include methyl glycolate, ethyl glycolate, propyl glycolate, butyl glycolate, methyl 2-hydroxypropionate, methyl 3-hydroxybutyrate, methyl 4-hydroxypentanoate and methyl 5-hydroxyhexanoate. Among them, methyl glycolate, ethyl glycolate and methyl 5-hydroxyhexanoate are especially preferred.

The ω-hydroxycarboxylic acids or esters (6) can be produced by known processes, such as hydrolysis and treatment with an alcohol of the corresponding lactone. In the present invention, those produced by known processes may be used, or alternatively, commercial products may be used either as they are or after purification, such as recrystallization and distillation.

In this step, the aliphatic amine (2) and ω-hydroxycarboxylic acid or ester (6), in an amount of 1 to 2.0 times by mole that of the aliphatic amine (2), are subjected to reaction for removal of a water or alcohol molecule in the absence of any solvent, and if desired, in the presence of a basic catalyst, such as $CH_3ONa$, KOH and NaOH, at 40° to 200° C., preferably 60° to 150° C. for 1 to 100 hrs, preferably 1 to 20 hrs, at a reduced pressure. The N-alkylcarbamylalkanol (4) can be obtained thereby.

In the reaction, the pressure is preferably reduced to 760–0.1 mmHg to effect dehydration.

When ω-hydroxycarboxylic acid is used, the aliphatic amine (2) and ω-hydroxycarboxylic acid in an amount of 1 to 2.0 times by mole that of the aliphatic amine (2) are subjected to reaction for removal of a water or alcohol molecule in the absence of any solvent at 100° to 250° C., preferably 150° to 200° C. for 5 to 100 hrs at a reduced pressure.

The N-alkylcarbamylalkanol (4) thus obtained may be used as it is in the subsequent step. If desired, however, it may be purified by recrystallization from a solvent, such as hexane, methanol, ethanol, acetone and chloroform.

The compound (1-3) according to the present invention can also be made by the following steps E and F in this order. The compound represented by the formula (1-4) can also be easily prepared by the following steps E and G in this order.

Step E

A step wherein an aliphatic amine represented by the general formula (7):

$$R^1-NH_2 \quad (7)$$

(wherein $R^1$ stands for the same meaning as defined above with respect to compound (1-3)). is reacted with glycolic acid or an ester thereof represented by the general formula (8):

$$HO-CH_2CO_2R^2 \quad (8)$$

(wherein $R^2$ stands for a hydrogen atom or a linear or branched alkyl group having 1 to 4 carbon atoms) to obtain an N-alkylglycolamide represented by the general formula (9):

(wherein $R^1$ stands for the same meaning as defined above with respect to compound (1-3)).

Step F

A step wherein the N-alkylglycolamide obtained in the step E and represented by the general formula (9) is reacted with a sulfating agent, and then neutralized with a basic substance selected from the group consisting of potassium hydroxide, potassium carbonate and potassium bicarbonate to obtain the compound represented by the aforementioned general formula (1-3).

Step G

A step wherein the N-alkylglycolamide obtained in the step E and represented by the general formula (9) is reacted with a sulfating agent, and then neutralized with a basic substance other than potassium-containing basic substances to obtain the compound represented by the aforementioned general formula (1-4).

These steps will now be described in detail.

Step E

This step is a step wherein the aliphatic amine represented by the above-mentioned general formula (7) [hereinafter referred to briefly as the "aliphatic amine (7)"] is reacted with glycolic acid or an ester thereof represented by the above-mentioned general formula (8) [hereinafter referred to briefly as "glycolic acid or an ester thereof (8)"] to obtain the N-alkylglycolamide represented by the above-mentioned general formula (9) [hereinafter referred to briefly as the "N-alkylglycolamide (9)"].

Specific examples of the aliphatic amine (7) include octylamine, decylamine, dodecylamine, tetradecylamine, hexadecylamine, octadecylamine, and isostearylamine, among which decylamine, dodecylamine and tetradecylamine are preferred, and dodecylamine is especially preferred.

Examples of the ester of glycolic acid include methyl, ethyl, propyl, and butyl esters thereof, among which methyl glycolate and ethyl glycolate are preferred particularly by reason of foaming properties and chemical stability.

In this step, the aliphatic amine (7) and glycolic acid or an ester thereof (8), the amount of which is 1 to 2.0 times in terms of mol as much as that of the former, are subjected to dehydration or dealcoholization in the absence of any solvents and, if necessary, in the presence of a basic catalyst such as $CH_3ONa$, KOH or NaOH at 40° to 200° C., preferably at 60° to 150° C., for 1 to 100 hours, preferably for 1 to 20 hours, to obtain the N-alkylglycolamide (9).

The pressure during the reaction is preferably reduced to 760 to 0.1 mmHg because dehydration is necessary.

The N-alkylglycolamide (9) thus obtained can be used as such in the next step, but, if necessary, may be recrystallized from a solvent such as hexane, methanol, ethanol, acetone or chloroform to effect purification thereof.

Step F

This step is a step wherein the N-alkylglycolamide (9) obtained in the step E is reacted with a sulfating agent, and then neutralized with a basic substance selected from the group consisting of potassium hydroxide, potassium carbonate or potassium bicarbonate to obtain the compound represented by the above-mentioned general formula (1-3) [hereinafter referred to briefly as the "compound (1-3)"].

Examples of the sulfating agent include chlorosulfonic acid, sulfuric anhydride, fuming sulfuric acid, concentrated sulfuric acid, and sulfamic acid, among which chlorosulfonic acid, sulfuric anhydride and sulfamic acid are preferred from the standpoint of reaction yield.

In this step, the sulfating agent is used in an amount 1 to 1.5 times in terms of mol as much as that of the N-alkylglycolamide (9), and the reaction therebetween is effected in a solvent such as dichloromethane, chloroform, 1,2-dichloroethane, dimethylformamide, dimethyl sulfoxide or dioxane, the amount of which is 0 to 10 times as much as that of the N-alkylglycolamide (9), at −50° to 80° C., preferably at −30° to 50° C., for 1 to 20 hours to obtain the corresponding sulfation product.

Additionally stated, the solvent must be purified into such a state as to be substantially free of water and alcohols. Although this sulfation can also be effected in the absence of any solvents, a countermeasure in an aspect of equipment is necessary because the viscosity of the reaction system is notably increased during the course of the reaction.

On the other hand, when the reaction temperature exceeds 80° C., side reactions such as cleavage of the amido group unfavorably proceed.

After the completion of the sulfation reaction, the solvent used in the reaction is distilled off if necessary. Additionally stated, the solvent may alternatively be distilled off after the following neutralization.

Subsequently, the sulfation product obtained by the foregoing reaction and the aforementioned basic substance, the amount of which is 0.9 to 1.5 times in terms of equivalent as much as that of the former, are subjected to a neutralization reaction in a solvent such as ethanol or methanol at −50° to 80° C. for 0.1 to 1 hour to obtain the compound (1-3).

The compound obtained by the above-mentioned neutralization reaction includes by-products such as the N-alkylglycolamide and an amine. The reaction product can be used as such according to a use, but may be purified through recrystallization, column chromatography, electrodialysis, extraction with a solvent, or the like if necessary to prepare a higher-purity product.

Step G

This step is a step wherein the N-alkylglycolamide (9) obtained in the step E is reacted with a sulfating agent, and then neutralized with a basic substance except for potassium-containing basic substances to obtain the compound represented by the aforementioned general formula (1-4) [hereinafter referred to briefly as the "compound (1-4)"].

The reaction of the N-alkylglycolamide (9) with the sulfating agent in this step can be effected in completely the same manner as in the step F.

Examples of the basic substance to be used in this step except for potassium-containing basic substances include hydroxides, carbonates and bicarbonates of alkali metals except for potassium and alkaline earth metals; ammonia; alkanolamines having 2 to 9 carbon atoms in total; alkylamines and alkenylamines having 1 to 22 carbon atoms in total; pyridine substituted with alkyl or alkenyl having 1 to 18 carbon atoms; and basic amino acids. Specific examples of the basic substance include inorganic alkalis such as sodium hydroxide, lithium hydroxide, barium hydroxide, sodium hydrogencarbonate and sodium carbonate, ammonia, monoethanolamine, diethanolamine, triethanolamine, methylamine, dimethylamine, trimethylamine, ethylamine, diethylamine, triethylamine, decylamine, dodecylamine, tetradecylamine, hexadecylamine, octadecylamine, and basic amino acids, among which ammonia, sodium hydroxide and triethanolamine are preferred. They may be used in the form of an aqueous solution thereof or an alcoholic solution thereof for neutralization of the sulfuric ester. The degree of neutralization can be arbitrarily set. Further, the conditions of the neutralization reaction, the purification treatment, etc. may be the same as in the step F.

The N-alkylcarbamylalkanol sulfate or the salt thereof (1-1) and (1-3) or the salt of N-alkylcarbamylalkanol sulfate (1-2) according to the present invention is a surfactant ensuring not only excellent performance in detergency and foaming power but also high safety, so that it is suitable for use in various detergents such as a shampoo, a detergent for the body and a detergent for tableware.

The detergent composition of the present invention contains the N-alkylcarbamylalkanol sulfate or the salt thereof (1-1), (1-3), or the salt of N-alkyl-carbamylalkanol sulfate (1-2) as an essential ingredient. The content thereof (the total content when two or more compounds are used) is preferably in the range of 1 to 70% by weight, still preferably in the range of 10 to 70% by weight based on the total weight of the composition.

When a detergent composition containing compound (1-3) further comprises compound (1-4), the blending proportion thereof is preferably in the following range in terms of weight ratio: compound (1-3)/compound (1-4)=100/1 to 1/100.

The detergent composition of the present invention may also contain ingredients used in a conventional detergent such as a shampoo, a detergent for the body and a detergent for tableware, as long as the effect of the present invention is not adversely affected. Additional ingredients that may be used in the detergent composition include silicone derivatives or aqueous emulsions thereof such as those disclosed in Japanese Patent Laid-Open No. 43,433/1993, cationic surfactants such as those disclosed in Japanese Laid-Open No. 172,133/1994; water-soluble cationic polymers, anionic surfactants, nonionic surfactants, amphoteric surfactants, dandruff removers, vitamin preparations, sterilizers, antiphlogisitics, preservatives, humectants such as propylene glycol, glycerol, diethylene glycol monoethyl ether, sorbitol and panthenol, colorants such as dyes and pigments, bactericides, emulsifiers and fragrances and other ingredients as disclosed in the ENCYCLOPEDIA OF SHAMPOO INGREDIENTS (Micelle Press, 1985).

The detergent composition of the present invention may further comprise a salt such as potassium chloride for the purpose of controlling the Krafft point thereof.

Examples of the silicone derivatives suitable for use in the present invention include the following silicone derivatives 1) to 9):

1) dimethylpolysiloxane

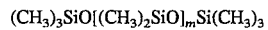

(m=3 to 20,000)

2) methylphenylpolysiloxane

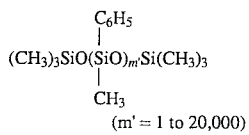

(m' = 1 to 20,000)

or

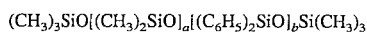

(wherein a+b=1 to 500)

3) polyether-modified silicone

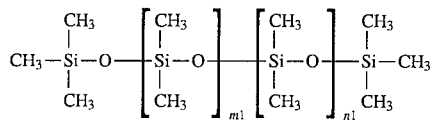

or

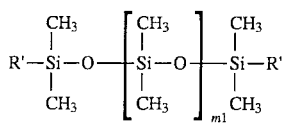

or

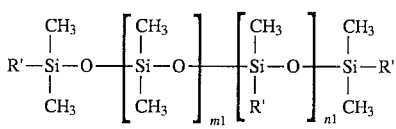

wherein

A: alkyl group having 1 to 12 carbon atoms or hydrogen atom $x_1$: 0~50  $y_1$: 0~50  ($x_1+y_1 \geq 1$)
$m_1$: 1~2000
$n_1$: 1~1000

4) epoxy-modified silicone

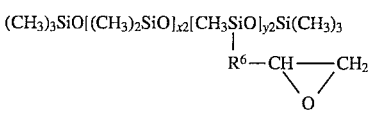

wherein $x_2$ is a number of 1 to 500, preferably 1 to 250, $y_2$ is a number of 1 to 50, preferably 1 to 30 and $R^6$ represents an alkylene group having 1 to 3 carbon atoms 5) fluorinated silicone

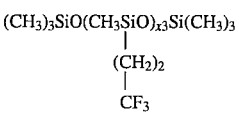

wherein $x_3$ is a number of 1 to 400, preferably 1 to 250

6) alcohol-modified silicone

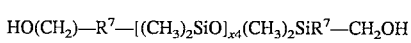

or $(CH_3)_3SiO[(CH_3)_2SiO]_{x4}(CH_3SiO)_{y4}Si(CH_3)_3$
|
$R^7$—CHOH
|
$CH_3$ wherein $x_4$ and $y_4$ are each a number of 1 to 500, preferably 1 to 200 and $R^7$ represents $C_{n'}H_{2n'}$ (wherein n'=0 to 4)

7) alkyl-modified silicone

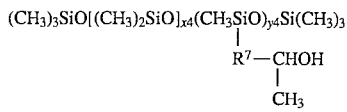

or

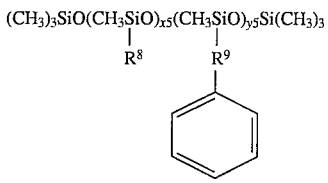

wherein $x_5$ and $y_5$ are each a number of 1 to 500, preferably 1 to 200, $R^8$ represents an alkyl group having 2 to 18 carbon atoms, $R^9$ represents $C_{n'}H_{2n'}$ (wherein n'=0 to 4), and $R^{10}$ represents an alkyl group having 10 to 24 carbon atoms 8) alkoxy-modified silicone

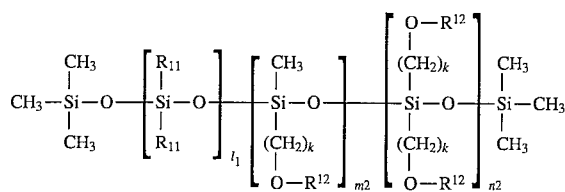

wherein $R^{11}$ represents a methyl group or a phenyl group, $l_1$ is a number of 1 to 3000, $m_2$ and $n_2$ are numbers satisfying the relation $m_2+n_2=1$ to 500, $R^{12}$ represents an alkyl group having 1 to 28 carbon atoms, preferably 12 to 22 carbon atoms, and k is an integer of 0 to 6, and 9) amine-modified silicone

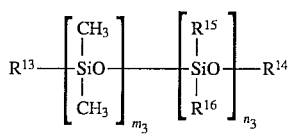

or

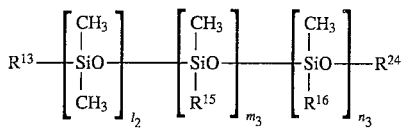

wherein $R^{13}$ represents a methyl group or a hydroxyl group; $R^{14}$ represents a methyl group or a hydrogen atom; $R^{15}$ represents an aminoalkyl group represented by the formula:

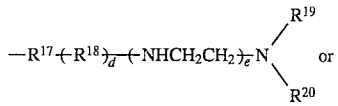

-continued

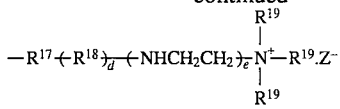

wherein $R^{17}$ represents a divalent hydrocarbon group, $R^{18}$ represents the group of —OCH$_2$CH$_2$—,

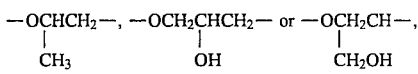

each of $R^{22}$ and $R^{20}$ represents a hydrogen atom or a monovalent hydrocarbon group, each of d and e is a number of 0 to 6, and $Z^-$ represents a halide ion or an organic anion;

$R^{16}$ represents a hydroxy group, a hydroxyalkyl group, an oxyalkylene group [i.e., a group represented by —(OA)—OH (wherein OA represents an oxyalkylene group)] or a polyoxyalkylene group [i.e., a group represented by —(OA)$_p$—OH (wherein OA represents an oxyalkylene group and p is an average addition mole number of alkylene oxide)]; and each of $l_2$, $m_3$ and $n_3$ is a number depending on the molecular weight.

Among them, especially preferred amine-modified silicones are those represented by the following general formula:

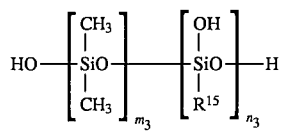

wherein $R^{15}$, $m_3$ and $n_3$ are defined above.

Among them, representative are those represented by the following formula:

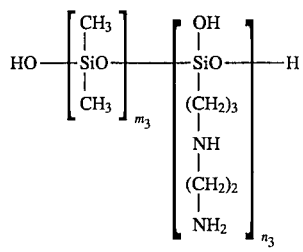

wherein $m_3$ and $n_3$ are defined above.

As the amine-modified silicone, those represented by the above formula and having an average molecular weight of about 3,000 to 100,000, and which are named Amodimethicone and described in the dictionary of CTFA (U.S., Cosmetic Ingredient Dictionary), 3rd edition, are preferred.

It is preferred that the above amine-modified silicone be used in the form of a water-base emulsion. Such a water-base emulsion can be obtained, for example, by performing an emulsion polymerization of a cyclic diorganopolysilocane and an organodialkoxysilane having an aminoalkyl group, and a hydroxy group, a hydroxyalkyl group, an oxyalkylene group or a polyoxyalkylene group, in the presence of a surfactant based on a quaternary ammonium salt together with water, in accordance with the process described in U.S. Pat. No. 4,228,054 (published on Oct. 14, 1980; assignee: Toray Silicone Co., Ltd.).

When the above amine-modified silicone is used in the form of a water-base emulsion, the content of the amine-modified silicone in the emulsion is generally in the range of 20 to 60% by weight, preferably 30 to 50% by weight.

Preferred water-base amine-modified silicone emulsions are commercially available, which include, for example, SM 8702C (produced by Toray Silicone Co., Ltd.) and DC 929 (produced by Dow Corning Corporation).

These silicone derivatives may be used individually or in combination of two or more, and incorporated in the detergent composition of the present invention in an amount of preferably 0.01 to 3% by weight, still more preferably 0.1 to 0.8% by weight.

The silicone derivatives 1) to 9) described above may be used as such or in the form of a silicone emulsion wherein a silicone derivative is dispersed in an aqueous medium with at least one surfactant, as an emulsifier, selected from the group consisting of a nonionic surfactant, an anionic surfactant, a cationic surfactant and an amphoteric surfactant. The silicone emulsion may be obtained by stirring and mixing the mixture comprising a silicone derivative and an aqueous medium or by an emulsion polymerization process of the silicone derivative. Examples of silicone emulsions which are put on the market include KM 880, KM 883, KM 884, KM 885, KM 886 and KM 887 (mfd. by Shin-Etsu Chemical Industries Co. Ltd.), TEX 100, TSW 831, TEX 150, TEX 154, TEX 170, TEX 152 and TEX 172 (mfd. by Toshiba Silicone Co. Ltd.) and BY22-007, BY22-029, BY22-019, BY22-034, BY22-020, BY22-009, BY22-008 and SM 5571 (mfd. by Toray Dow Corning Silicone Co. Ltd.).

The cationic surfactants for use in the present invention include, for example, quaternary ammonium salts represented by the following general formulae (7) and (8):

 (7)

 (8)

wherein at least one of $R^{21}$, $R^{22}$, $R^{23}$ and $R^{24}$ represents an alkyl or alkenyl group that may be substituted with an alkoxy, alkenyloxy, alkanoylamino or alkenoylamino group, having 8 to 28 carbon atoms in total, and the remainings of $R^{21}$, $R^{22}$, $R^{23}$ and $R^{24}$ represent a benzyl group, an alkyl or hydroxyalkyl group having 1 to 5 carbon atoms; $R^{25}$ represents an alkylene group having 2 or 3 carbon atoms; Z represents a halide ion or an organic anion; and $n_4$ is a number of 1 to 20. Among the above cationic surfactants, quaternary ammonium salts represented by the general formula (7) are preferred. Further, among the quaternary ammonium salts represented by the general formula (7), branched quaternary ammonium salts represented by the following general formulae (9) to (11) are particularly preferred.

 (9)

-continued

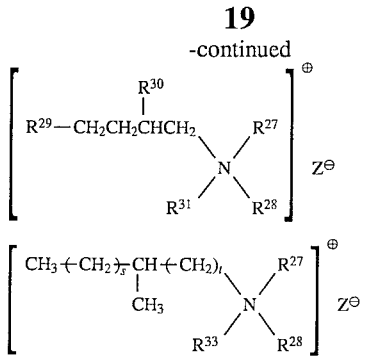

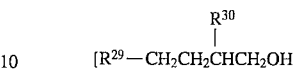

wherein $R^{26}$ is a branched alkyl group represented by the formula (a):

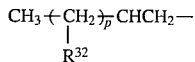

(wherein
$R^{32}$ represents a methyl group or an ethyl group, and p is an integer selected so as to allow the total number of carbon atoms in the alkyl group to be 8–16, or a linear alkyl group represented by the formula (b) : $CH_3$—$(CH_2)_{\overline{q}}$ (b) (wherein q is an integer of 7 to 15); each of $R^{27}$ and $R^{28}$ represents a benzyl group or an alkyl or hydroxyalkyl group having 1 to 3 carbon atoms; each of $R^{29}$ and $R^{30}$ represents an alkyl group having 2 to 12 carbon atoms; $R^{31}$ represents a group of

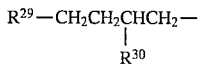

or an alkyl group having 1 to 3 carbon atoms; $R^{33}$ represents a group of

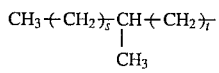

or an alkyl group having 1 to 3 carbon atoms; s and t are integers of 2 to 14 and 3 to 11, respectively, and the sum of s and t is 9 to 21; and Z represents a halide ion or an organic anion.

The surfactant, i.e., the branched quaternary ammonium salt, represented by the general formula (9) has a branching ratio of $R^{26}$ [formula (a)/formula (a)+formula (b)] of 10 to 100%, and those having a branching ratio of 10 to 50% are particularly preferred.

The surfactant represented by the general formula (9) is synthesized, for example, from an oxo alcohol having 8 to 16 carbon atoms as a starting compound. Examples thereof include a dialkyldimethylammonium salt, a dialkylmethylhydroxyethylammonium salt and a dialkylmethylbenzylammonium salt, each having an alkyl group derived from an oxo alcohol.

Although one alkyl group of $R^{26}$ has 8 to 16 carbon atoms in the general formula (9), those wherein a given distribution, especially the following distribution, is present with respect to the carbon atom number of one alkyl group of $R^{26}$, among surfactants represented by the general formula (9), are preferably used in the present invention:

$C_8$–$C_{11}$: 5% or less
$C_{12}$: 10–35%
$C_{13}$: 15–40%
$C_{14}$: 20–45%
$C_{15}$: 5–30%
$C_{16}$: 5% or less Specific examples of the above surfactant, i.e., the branched quaternary ammonium salt, include a dialkyldimethylammonium chloride having an alkyl group of 8 to 16 carbon atoms and a branching ratio of 10 to 50%.

The branched quaternary ammonium salt represented by the general formula (10) is generally synthesized from a Guerbet alcohol $$[R^{29}-CH_2CH_2\overset{R^{30}}{\underset{|}{C}}HCH_2OH$$

(wherein $R^{29}$ and $R^{30}$ are each defined above)] having 8 to 28 carbon atoms, as a starting compound. Preferred examples of the branched quaternary ammonium salts include alkyltrimethylammonium salts, alkyldimethylbenzylammonium salts, dialkyldimethylammonium salts, dialkylmethylhydroxyethylammonium salts and dialkylmethylbenzylammonium salts, each having an alkyl group derived from a Guerbet alcohol. Among them, especially preferred examples include 2-decyltetradecyltrimethylammonium chloride, 2-dodecylhexadecyltrimethylammonium chloride, di-2-hexyldecyldimethylammonium chloride and di-2-octyldodecyldimethylammonium chloride.

Preferred examples of the methyl-branched quaternary ammonium salts represented by the general formula (11) are those having s and t values totaling 15.

Specific examples of Z as a counter ion for each of the quaternary ammonium salts represented by the general formulae (7), (8), (9), (10) and (11) include halide (such as chloride, iodide and bromide) ions; and organic anions, such as methosulfate, ethosulfate, methophosphate and ethophosphate.

The above cationic surfactants may be used either individually or in combination of two or more, and incorporated in the detergent composition of the present invention preferably in an amount of 0.05 to 10% by weight.

The water-soluble cationic polymer for use in the present invention is a water-soluble polymer either comprising a polymer chain having an amino group or an ammonium group bonded thereto or comprising at least a dimethyldiallylammonium halide as a structural unit. Examples thereof include cationized cellulose derivatives, cationic starches, cationized guar gum derivatives, copolymers of quaternary diallylammonium salt and acrylamide, and quaternary polyvinylpyrrolidone derivatives.

As the cationized cellulose derivatives, for example, those represented by the following general formula (12) are preferred:

In the formula (12), A represents an anhydroglucose unit residue, f is a number of 50 to 20000, and $R^{34}$ is a substituent represented by the following general formula (13):

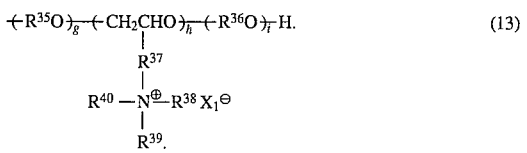

In the formula (13), $R^{35}$ and $R^{36}$ may be the same or different from each other and each represents an alkylene group having 2 or 3 carbon atoms; g is a number of 0 to 10; h is a number of 0 to 3; i is a number of 0 to 10; $R^{37}$ represents an alkylene or hydroxyalkylene group having 1 to 3 carbon atoms; $R^{38}$, $R^{39}$ and $R^{40}$ may be the same or different from one another and each represents an alkyl, aryl or aralkyl group having 1 to 10 carbon atoms, or may form a heterocycle together with the nitrogen atom in the formula (13); and $X_1^-$ represents an anion, e.g., chloride ion, bromide ion, iodide ion, sulfonate ion, methylsulfate ion or nitrate ion.

Similar to the cationized cellulose derivative represented by the formula (12), those having a divalent anion such as sulfate ion, and others having a trivalent anion such as phosphate ion, are cited. In such cationized cellulose derivatives, the valence of anion and the valence of cation are identical, as well.

As the cationized cellulose derivative used in the present invention, those represented by the formula (12) which have the degree of cationization, that is, the average value of h per anhydroglucose unit, of 0.01 to 1 are preferable and those represented by the formula (12) which have the degree of cationization of 0.02 to 0.5 are still more preferable. Such cationized cellulose derivatives have a sum of g and i (average value) of 1 to 3. A degree of cationization of less than 0.01 is not satisfactory. Although those having a degree of cationization greater than 1 may be used, the synthesis thereof are disadvantageous from the viewpoint of the reaction yield. It is preferred that the average molecular weight of the cationized cellulose derivative to be employed in the present invention be in the range of about 100,000 to 3,000,000.

As the cationic starches, those represented by the following general formula (14) are preferred:

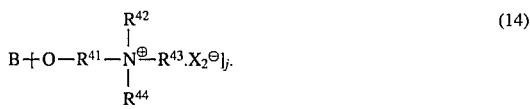

In the formula (14), B represents a starch residue; $R^{41}$ represents an alkylene group or a hydroxyalkylene group; $R^{42}$, $R^{43}$ and $R^{44}$ may be the same or different from one another and each represents an alkyl, aryl or aralkyl group having 1 to 10 carbon atoms, or may form a heterocycle together with the nitrogen atom in the formula; $X_2^-$ represents an anion, e.g., chloride ion, bromide ion, iodide ion, sulfonate ion, methylsulfate ion or nitrate ion; and j is a positive number.

Similar to the cationic starch represented by the formula (14), those having a divalent anion such as sulfate ion, and others having a trivalent anion such as phosphate ion, are cited. In such cationic starches, the valence of anion and the valence of cation are identical.

As the cationic starch to be used in the present invention, those represented by the formula (14) which have the degree of cationization of 0.01 to 1, that is, those in which 0.01 to 1 cation group is introduced per anhydroglucose unit, are preferred, and those in which 0.02 to 0.5 cation group is introduced per anhydroglucose unit are still more preferred. A degree of cationization less than 0.01 is not satisfactory. Although those having a degree of cationization greater than 1 may be used, the synthesis thereof are disadvantageous from the viewpoint of the reaction yield.

As the cationized guar gum derivatives, those represented by the following general formula (15) are preferred:

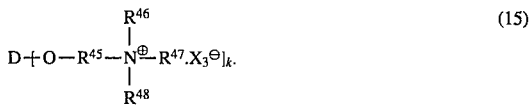

In the formula (15), D represents a guar gum residue; $R^{45}$ represents an alkylene or hydroxyalkylene group; $R^{46}$, $R^{47}$ and $R^{48}$ may be the same or different from one another and each represents an alkyl, aryl or aralkyl group having 1 to 10 carbon atoms, or may form a heterocycle together with the nitrogen atom in the formula; $X_3^-$ represents an anion, e.g., chloride ion, bromide ion, iodide ion, sulfonate ion, methylsulfate ion or nitrate ion; and k is a positive number.

Similar to the cationized guar gum derivative represented by the formula (15), those having a divalent anion such as sulfate ion, and others having a trivalent anion such as phosphate ion, are cited. In such cationized guar gum derivatives, the valence of anion and the valence of cation are identical, as well.

As the cationized guar gum derivative to be used in the present invention, those represented by the formula (15) which have the degree of cationization of 0.01 to 1, that is, those in which 0.01 to 1 cation group is introduced per glucose unit, are preferred, and those in which 0.02 to 0.5 cation group is introduced per glucose unit are still more preferred. This type of cationic polymer is described in, for example, U.S. Pat. Nos. 4,298,494 (published on Nov. 3, 1981; assignee: UNILEVER NV), 5,037,818 (published on Aug. 6, 1991; assignee: UNILEVER NV, CHESEBROUGH PONDS INC) and 4,364,837 (published on Dec. 21, 1982; assignee: LEVER BROTHERS CO.), and is commercially available under the trademark of Jaguar (product by Celanese Stein Hall).

As the cationic copolymers of quaternary diallylammonium salt and acrylamide, those represented by the following general formulae (16) and (17) are preferred:

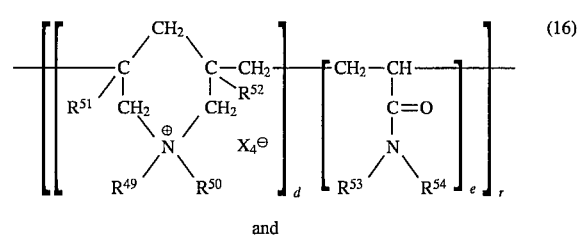

and

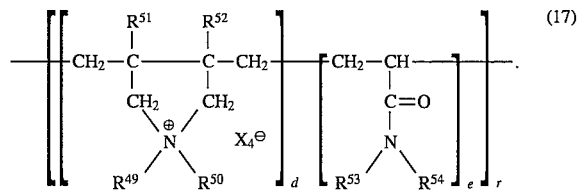

In the formulae (16) and (17), $R^{49}$ and $R^{50}$ may be the same or different from each other and each represents a hydrogen atom, an alkyl group having 1 to 18 carbon atoms, a phenyl group, an aryl group, a hydroxyalkyl group, a carbamylalkyl group, a cyanoalkyl group, an alkoxyalkyl group or a carboalkoxyalkyl; $R^{51}$, $R^{52}$, $R^{53}$ and $R^{54}$ may be the same or different from one another and each represents a hydrogen atom, a lower alkyl group having 1 to 3 carbon atoms or a phenyl group; $X_4^-$ represents an anion, e.g., chloride ion, bromide ion, iodide ion, sulfonate ion, methylsulfate ion or nitrate ion; d is a number of 1 to 50; e is a number of 0 to 50; and r is a number of 150 to 8000.

Similar to the copolymer of quaternary diallylammonium salt and acrylamide represented by the formulae (16) or (17), those having a divalent anion such as sulfate ion, and others having a trivalent anion such as phosphate ion, are cited. In such copolymers of quaternary diallylammonium salt and acrylamide, the valence of anion and the valence of cation are identical, as well.

As the copolymer of quaternary diallylammonium salt and acrylamide to be used in the present invention, those having an average molecular weight of about 30,000 to 2,000,000 are preferred, and those having an average molecular weight of 100,000 to 1,000,000 are still more preferred.

As the quaternary polyvinylpyrrolidone derivatives, those represented by the following formula (18) are preferred:

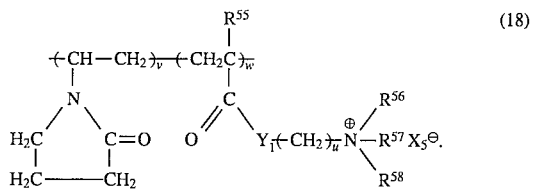

In the formulae (18), $R^{55}$ represents a hydrogen atom or an alkyl group having 1 to 3 carbon atoms; $R^{56}$, $R^{57}$ and $R^{58}$ may be the same or different from one another and each represents a hydrogen atom or an alkyl, hydroxyalkyl, carbamylalkyl, cyanoalkyl, alkoxyalkyl or carboalkoxyalkyl group having 1 to 4 carbon atoms; $Y_1$ represents an oxygen atom or an NH group forming an amide bond; $X_5^-$ represents an anion, e.g., chloride ion, bromide ion, iodide ion, sulfonate ion, alkyl sulfate ion having an alkyl group of 1 to 4 carbon atoms or nitrate ion; u is an integer of 1 to 10; and v+w is a number of 20 to 8000.

Similar to the quaternary polyvinylpyrrolidone derivative represented by the formula (18), those having a divalent anion such as sulfate ion, and others having a trivalent anion such as phosphate ion, are cited. In such quaternary polyvinylpyrrolidone derivatives, the valence of anion and the valence of cation are identical, as well.

As the quaternary polyvinylpyrrolidone derivative to be used in the present invention, those having an average molecular weight of 10,000 to 2,000,000 are preferred, and those having an average molecular weight of 50,000 to 1,500,000 are still more preferred.

The above cationic polymers may be used either individually or in combination of two or more, and are incorporated into the detergent composition of the present invention in an amount of preferably 0.01 to 3% by weight, still more preferably 0.1 to 0.8% by weight.

Examples of the anionic surfactants for use in the present invention include alkyl sulfates, alkyl ether sulfates, alkyl sulfonates and sulfosuccinates.

Examples of the nonionic surfactants for use in the present invention include alkyl glycosides represented by the following formula (19), amine oxides, oxyalkylene alkyl ethers, monoglycerides and mono- and dialkanolamides:

wherein $R^{59}$ represents a linear or branched, alkyl or alkenyl group having 8 to 18 carbon atoms, or an alkylphenyl group having an alkyl group of 8 to 18 carbon atoms; G represents a reducing sugar residue having 5 to 6 carbon atoms; x is a number of 0 to 20; and y is a number of 1 to 10.

Examples of the amphoteric surfactants for use in the present invention include (long-chain alkyl)-dimethylcarboxy-methyl betaines.

Examples of the humectants for use in the present invention include glycerol, propylene glycol and ethylene glycol.

The N-alkylcarbamylalkanol sulfates and salts thereof according to the present invention ensures not only low irritancy to the skin but also excellent foaming power and detergency. Therefore, the detergent composition of the present invention containing the N-alkylcarbamylalkanol sulfate and/or the salt thereof is useful as detergents for hair, skin, tableware, etc.

The detergent composition of the present invention can be prepared according to any customary method. For example, predetermined amounts of the compound (1-3), the compound (1-4), and an optional ingredient(s) used in conventional detergents such as shampoos and body detergents, provided that the effect of the present invention is not spoiled thereby, are weighed out, fed into equipment capable of agitation and mixing, such as a blender vessel, and then mixed with each other while being heated or cooled to prepare a detergent composition. In this case, the heating temperature, the cooling temperature, the heating or cooling rate, the agitation speed, and the agitation time are not particularly limited.

The pearly luster of the composition containing (1-3) becomes more beautiful according to a method wherein they are once heated to a temperature of at least the Krafft point of compound (1-3) and then cooled. Alternatively, a pearly aqueous dispersion of the compound (1-3) may be preliminarily prepared, and then mixed with other optional ingredient(s). Further alternatively, crystals of the compound (1-3) may be mixed with other optional ingredient(s).

The detergent composition of the present invention is preferably adjusted with a known acidic or alkaline agent to a pH of 3 to 10, especially preferably to a pH of 5 to 8.

The detergent composition containing compound (1-3) of the present invention can be formed into a paste, a gel, or a liquid by using a viscosity modifier or the like according to its purpose. Further, it may comprise a cationic conditioning agent blended therein to be suitable as a hair detergent in the form of a rinse-in shampoo or the like.

The detergent composition containing compound (1-3) of the present invention has excellent detergency, excellent foaming properties, low irritating properties, a pearly luster, and excellent resistance to hard water to be useful as a hair detergent, a body detergent, etc.

The detergent composition containing compound (1-3) of the present invention is inherently provided with a pearly luster even without incorporation of another substance to manifest a pearly luster.

EXAMPLES

Hereinbelow, the present invention will be described in greater detail with reference to the following Examples, which should not be construed as limiting the scope of the invention. % in Examples is by weight unless otherwise specified.

EXAMPLE 1

Synthesis of Sodium Salt of N-dodecyl-1-sulfoxyacetamide

(1) Synthesis of N-dodecylglycolamide 181.4 g (1.0 mol) of dodecylamine, 104.1 g (1.0 mol) of ethyl glycolate and 7.5 g (40 mmol) of a methanol solution containing 28% sodium methylate were fed into a 500-ml four-necked flask equipped with a stirrer and a thermometer. The obtained mixture was stirred under a stream of nitrogen gas, and the temperature thereof was elevated to 100° C. At this temperature, the reaction mixture was stirred for 2 hr while distilling off formed methanol. The obtained reaction mixture was dissolved in 500 ml of ether at room temperature. The ether solution thus obtained was transferred to a separatory funnel, and washed with water. The ether phase was separated, and concentrated. The solid remaining after concentration was dried in a reduced pressure to thereby obtain 182.3 g of white powdery N-dodecylglycolamide (yield: 74.9%). The hydroxyl value of this N-dodecylglycolamide was 229.4 (calculated value: 230.5).

The infrared absorption spectrum data and $^1$H-NMR spectrum data thereof were as follows:

Infrared Absorption Spectrum (KBr Tablet Method)

3334 (O—H stretching), 3262 (N—H stretching), 2920, 2854 (C—H stretching), 1638 (C=O stretching) cm$^{-1}$ $^1$H-NMR Spectrum (δ, ppm) in CDCl$_3$ a: 0.89 ppm (t, 3H)
b: 1.30 ppm (m, 18H)
c: 1.55 ppm (m, 2H)
d: 3.27 ppm (q, 2H)
e: 7.02 ppm (b, 1H)
f: 4.02 ppm (s, 2H)
g: 5.10 ppm (b, 1H)

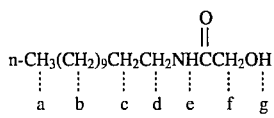

(2) Synthesis of Sodium Salt of N-dodecyl-1-sulfoxyacetamide 35.5 g (146 mmol) of the N-dodecylglycolamide synthesized in the above step (1) was put in a 500-ml four-necked flask equipped with a stirrer, a dropping funnel, a condenser tube and a thermometer. Next, 350 ml of chloroform was put in the flask to thereby dissolve the N-dodecylglycolamide in the chloroform. While stirring the obtained chloroform solution at room temperature under a stream of nitrogen gas, 17.9 g (153 mmol) of chlorosulfonic acid was dropwise added thereto over a period of about 30 min. During the period, the flask was sometimes cooled in a water bath to prevent the reaction temperature from exceeding 40° C. After the completion of the dropwise addition, the mixture thus obtained was stirred at 30° C. for 2 hrs. The reaction mixture thus obtained was poured into 500 ml of an ice water/n-butanol mixture containing 150 g of ice water. The obtained mixture was transferred to a separatory funnel, the funnel was vigorously shaked, and then an organic phase was separated. This organic phase was neutralized with a 10% aqueous sodium hydroxide solution, followed by solvent removal by distillation under reduced pressure and drying of the residue. Thus, 39.8 g of white powdery sodium salt of N-dodecyl-1-sulfoxyacetamide was obtained (yield: 78.9%). The infrared absorption spectrum data, $^1$H-NMR spectrum data and mass spectrum data thereof were as follows:

Infrared Absorption Spectrum (KBr Tablet Method)

3346 (N—H stretching), 2926, 2854 (C—H stretching), 1659 (C=O stretching), 1251, 1070 (S=O stretching) cm$^{-1}$ $^1$H-NMR spectrum (δ, ppm) in CDCl$_3$ a: 0.57 ppm (t, 3H)
b: 0.97 ppm (m, 18H)
c: 1.21 ppm (m, 2H)
d: 2.90 ppm (t, 2H)
e: 4.15 ppm (s, 2H)

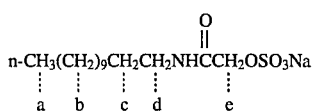

Mass Spectrum (Fab Ionization Method)

368: (M+Na)$^+$
266: (M+H—SO$_3$)$^+$
226: (M—OSO$_3$Na )$^+$

EXAMPLE 2

Synthesis of Ammonium Salt of N-dodecyl-1-sulfoxyacetamide

35.5 g (146 mmol) of the N-dodecylglycolamide synthesized in the step (1) of above Example 1 was put in a 1-l four-necked flask equipped with a stirrer, a dropping funnel, a condenser tube and a thermometer. Next, 500 ml of chloroform was put in the flask to thereby dissolve the N-dodecylglycolamide in the chloroform. While stirring the obtained chloroform solution at room temperature under a stream of nitrogen gas, 17.9 g (153 mmol) of chlorosulfonic acid was dropwise added thereto over a period of about 40 min. During the period, the flask was sometimes cooled in a water bath to prevent the reaction temperature from exceeding 40° C. After the completion of the dropwise addition, the mixture thus obtained was stirred at 25° to 30° C. for 2 hrs. The reaction mixture thus obtained was poured into 600 ml of an ice water/n-butanol mixture containing 300 g of ice water. The obtained mixture was transferred to a separatory funnel, the funnel was vigorously shaked, and then an organic phase was separated. This organic phase was neutralized with 10% aqueous ammonia, followed by solvent removal by distillation under reduced pressure and drying the residue. Thus, 41.4 g of white powdery ammonium salt of N-dodecyl-1-sulfoxyacetamide was obtained (yield: 83.3%). The anionic surfactant purity thereof was found to be 97.7% by titration according to the Epton method. The infrared absorption spectrum data thereof were as follows:

Infrared Absorption Spectrum (KBr Tablet Method)

3340 (N—H stretching), 2925, 2855 (C—H stretching), 1655 (C=O stretching), 1245, 1071 (S=O stretching) cm$^{-1}$

EXAMPLE 3

Synthesis of Sodium Salt of N-dodecyl-N-methyl-1-sulfoxyacetamide

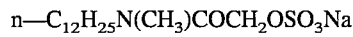

42.7 g (214 mmol) of dodecylmethylamine, 22.5 g (216 mmol) of ethyl glycolate and 2.1 g (0.7 mmol) of a methanol solution containing 28% sodium methylate were fed into a 200-ml four-necked flask equipped with a stirrer, a condenser tube and a thermometer. The obtained mixture was stirred under a stream of nitrogen gas, and the temperature thereof was elevated to 80° C. At this temperature, the mixture was stirred for 3 hrs while distilling off formed methanol. The temperature of the obtained reaction mixture was brought to room temperature, and then the reaction mixture was dissolved in 300 ml of ether. The ether solution thus obtained was transferred to a separatory funnel, and washed with water. The ether phase was separated, and concentrated. The liquid remaining after concentration was removed by distillation under reduced pressure and the residue was dried to thereby obtain N-dodecyl-N-methylglycolamide.

This amide was put in a 500 ml four-necked flask equipped with a stirrer, a dropping funnel, a condenser tube and a thermometer. Next, 300 ml of chloroform was put in the flask to thereby dissolve the N-dodecyl-N-methylglycolamide in the chloroform. While stirring the obtained chloroform solution at room temperature under a stream of nitrogen gas, 26.2 g (225 mmol) of chlorosulfonic acid was dropwise added thereto over a period of about 30 min. During the period, the flask was sometimes cooled in a water bath to prevent the reaction temperature from exceeding 30° C. After the completion of the dropwise addition, the obtained mixture was stirred at 25° to 30° C. for 1 hr. The obtained reaction mixture was poured into 400 ml of an ice water/n-butanol mixture containing 200 g of ice water. The obtained mixture was transferred to a separatory funnel, the funnel was vigorously shaken, and then an organic phase was separated. This organic phase was neutralized with a 10% aqueous sodium hydroxide solution, followed by solvent removal by distillation under reduced pressure and drying the residue. Thus, 34.0 g of white powdery sodium salt of N-dodecyl-N-methyl-1-sulfoxyacetamide was obtained (yield: 44.1%). The anionic surfactant purity thereof was found to be 99.4% by titration according to the Epton method. The infrared absorption spectrum data, $^1$H-NMR spectrum data and mass spectrum data thereof were as follows:

Infrared Absorption Spectrum (KBr Tablet Method)
2926, 2854 (C—H stretching), 1655, 1647 (C=O stretching), 1263, 1224, 1035 (S=O stretching) cm$^{-1}$ $^1$H-NMR spectrum ($\delta$, ppm) in CDCl$_3$ a: 0.59 ppm (t, 3H)

b: 1.00 ppm (m, 18H)

c: 1.22 ppm (m, 2H)

d: 3.01 ppm (m, 2H)

e: 2.60 ppm (s, 1.4H), 2.69 ppm (s, 1.6H)

f: 4.39 ppm (s, 2H)

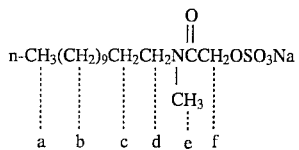

Mass Spectrum (Fab Ionization Method)

382: (M+Na)$^+$

280: (M+H—SO$_3$)$^+$

240: (M—OSO$_3$Na)$^+$

EXAMPLE 4

Synthesis of Sodium Salt of N-dodecyl-5-sulfoxyhexanamide (1) Synthesis of N-dodecyl-5-hydroxyhexanamide 384.20 g (2.0727 mol) of dodecylamine was fed into a 2-l four-necked flask equipped with a stirrer, a dropping funnel and a thermometer, and heated to 90° C. Then, 236.58 g (2.0727 mol) of ε-caprolactone was dropwise added to the dodecylamine over a period of about 0.5 hr. During this period, the temperature of the reaction system was maintained at 90° to 100° C. The reaction mixture was further stirred at 100° C. for 5 hrs. The obtained crude product having a temperature of its melting point or above was dropwise added to 2.1 l of hexane to crystallize. Thus, 509.53 g of N-dodecyl-5-hydroxyhexanamide was obtained (yield: 82%). The hydroxyl value thereof was 182.0 (calculated value: 187.33) and the infrared absorption spectrum data thereof were as follows:

Infrared Absorption Spectrum (KBr Tablet Method)
3316 (O—H stretching), 2926, 2854 (C—H stretching), 1635 (C=O stretching) cm$^{-1}$ (2) Synthesis of Sodium Salt of N-dodecyl-5-sulfoxyhexanamide 460.26 g (1.5368 mol) of the N-dodecyl-5-hydroxyhexanamide obtained in the above step (1) was put in a 5-l round-bottomed flask equipped with a stirrer, a dropping funnel, a condenser tube and a thermometer. Next, 2 l of chloroform was put in the flask to thereby dissolve the N-dodecyl-5-hydroxyhexanamide in the chloroform. While stirring the obtained chloroform solution at room temperature under a stream of nitrogen gas, 189 g (1.62 mol) of chlorosulfonic acid was dropwise added thereto over a period of about 1 hr. During the period, the temperature of the reaction system was maintained at 10° to 20° C. Thereafter, the obtained mixture was further stirred at room temperature for 1 hr. The obtained reaction mixture was poured into 1 l of an ice water/n-butanol mixture containing 300 ml of ice water. The obtained mixture was stirred for about 10 min, and then transferred to a separatory funnel. An organic phase was separated. This organic phase was neutralized with a 30% aqueous sodium hydroxide solution to adjust the pH thereof to 7. Chloroform and butanol were distilled off from the organic phase under reduced pressure. The remaining solid was washed with 2 l of acetone to obtain 575.06 g of sodium salt of N-dodecyl-5-sulfoxyhexanamide (yield: 93%). The infrared absorption spectrum data, $^1$H-NMR spectrum data and mass spectrum data of the obtained compound were as follows:

Infrared Absorption Spectrum (KBr Tablet Method)
3338 (N—H stretching), 2925, 2855 (C—H stretching), 1640 (C=O stretching), 1200, 1069 (S=O stretching) cm$^{-1}$ $^1$H-NMR spectrum ($\delta$, ppm) in D$_2$O a: 0.93 ppm (t, 3H)

b: 1.40 ppm (b, 18H)

c: 1.50 ppm (m, 2H)

d: 3.18 ppm (t, 2H)

e: 2.30 ppm (t, 2H)

f: 1.68 ppm (m, 6H)

g: 4.09 ppm (t, 2H)

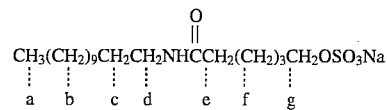

Mass Spectrum (Fab Ionization Method)

424: (M+Na)$^+$

322: (M+H—SO$_3$)$^+$

282: (M—OSO$_3$Na)$^+$

EXAMPLE 5

Synthesis of Ammonium Salt of N-dodecyl-5-sulfoxyhexanamide 600.0 g (2.0 mol) of the N-dodecyl-5-hydroxyhexanamide synthesized in step (1) of the above Example 4 was put in a 5-l four-necked flask equipped with a stirrer, a dropping funnel, a condenser tube and a thermometer. Next, 2 l of chloroform was put in the flask to thereby dissolve the N-dodecyl-5-hydroxyhexanamide in the chloroform. While stirring the obtained chloroform solution at room temperature under a stream of nitrogen gas, 270.4 g (2.5 mol) of chlorosulfonic acid was dropwise added thereto over a period of about 1 hr. During the period, the flask was sometimes cooled in a water bath to prevent the reaction temperature from exceeding 40° C. After the completion of the dropwise addition, the obtained mixture was stirred at 25° to 30° C. for 2 hrs. The obtained reaction mixture was poured into 2 l of an ice water/n-butanol mixture containing 1 kg of ice water. The obtained mixture was transferred to a separatory funnel, the funnel was vigorously shaked, and then an organic phase was separated. This organic phase was neutralized with 10% aqueous ammonia, followed by solvent removal by distillation under reduced pressure and drying the residue. Thus, 713.2 g of white powdery ammonium salt of N-dodecyl-5-sulfoxyhexanamide was obtained (yield: 90.0%). The anionic surfactant purity thereof was found to be 99.9% by titration according to the Epton method. The infrared absorption spectrum data thereof were as follows:

Infrared Absorption Spectrum (KBr Tablet Method)

3334, 3214 (N—H stretching), 2926, 2854 (C—H stretching), 1641 (C=0 stretching), 1209, 1065, 1044 (S=0 stretching) cm$^{-1}$

EXAMPLE 6

Synthesis of Sodium Salt of N-decyl-3-sulfoxybutyramide (1) Synthesis of N-decyl-3-hydroxybutyramide 535.7 g (3.41 mol) of n-decylamine was fed into a 2-l round-bottomed flask equipped with a stirrer, a dropping funnel and a thermometer, and heated to 80° C. while stirring under a stream of nitrogen gas. Then, from the dropping funnel, 293.2 g (3.41 mol) of γ-butyrolactone was introduced over a period of about 1 hr. During this period, the temperature of the reaction mixture elevated to about 100° C. due to exothermic reaction. The obtained reaction mixture was further stirred at 100° C. for 5 hrs. The obtained crude product having a temperature of its melting point or above was dropwise added to 3 l of hexane to crystallize. Thus, 767.9 g of N-decyl-3-hydroxybutyramide was obtained (yield: 89.2%). The hydroxyl value thereof was 228.6 (calculated value: 230.5). The infrared absorption spectrum data and $^1$H-NMR spectrum data thereof were as follows:

Infrared Absorption Spectrum (KBr Tablet Method)

3304 (O—H stretching), 3104 (N—H stretching), 2924, 2856 (C—H stretching), 1642 (C=0 stretching) cm$^{-1}$ $^1$H-NMR Spectrum (δ, ppm) in CDCl$_3$ a: 0.72 ppm (t, 3H)

b: 1.12 ppm (m, 14H)

c: 1.33 ppm (m, 2H)

d: 3.05 ppm (q, 2H)

e: 6.10 ppm ( b, 1H)

f: 2.18 ppm (t, 2H)

g: 1.70 ppm (m, 2H)

h: 3.50 ppm (t, 2H)

i: 3.64 ppm (b, 1H)

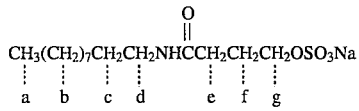

(2) Synthesis of Sodium Salt of N-decyl-3-sulfoxybutyramide 750.9 g (2.97 mol) of the N-decyl-3-hydroxybutyramide synthesized in the above step (1) was put in a 5-l round-bottomed flask equipped with a stirrer, a dropping funnel, a condenser tube and a thermometer. Next, 3 l of chloroform was put in the flask to thereby dissolve the N-decyl-3-hydroxybutyramide in the chloroform. While stirring the obtained chloroform solution at room temperature under a stream of nitrogen gas, 363.5 g (3.12 mol) of chlorosulfonic acid was dropwise added thereto over a period of about 4 hrs. During the period, the flask was cooled in a water bath to prevent the reaction temperature from exceeding 40° C. Thereafter, the obtained mixture was further stirred at 20° C. for 2 hrs. The obtained reaction mixture was poured into 3 l of an ice water/n-butanol mixture containing 1000 g of ice water. The obtained mixture was stirred for about 10 min, and then transferred to a separatory funnel. An organic phase was separated. This organic phase was neutralized with a 20% aqueous sodium hydroxide solution to adjust the pH thereof to 7. Chloroform and butanol were distilled off from the organic phase under reduced pressure. The remaining solid was washed with 3 l of ethanol to obtain 843.4 g of sodium salt of N-decyl-3-sulfoxybutyramide (yield: 82.2%). The infrared absorption spectrum data, $^1$H-NMR spectrum data and mass spectrum data of the obtained compound were as follows:

Infrared Absorption Spectrum (KBr Tablet Method)

3340 (N—H stretching), 2926, 2854 (C—H stretching), 1638 (C=0 stretching), 1206, 1071 (S=0 stretching) cm$^{-1}$ $^1$H-NMR Spectrum (δ, ppm) in D$_2$O a: 0.88 ppm (t, 3H)

b: 1.30 ppm (m, 14H)

c: 1.50 ppm (m, 2H)

d: 3.20 ppm (t, 2H)

e: 2.37 ppm (t, 2H)

f: 1.96 ppm (m, 2H)

g: 4.10 ppm (t, 2H)

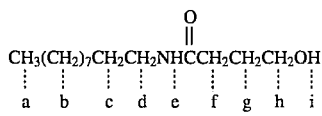

Mass Spectrum (Fab Ionization Method)

368: (M+Na)$^+$

266: (M+H—SO$_3$)$^+$

226: (M—OSO$_3$Na)$^+$

EXAMPLE 7

Synthesis of Sodium Salt of N-tetradecyl-3-sulfoxybutyramide (1) Synthesis of N-tetradecyl-3-hydroxybutyramide 508.19 g (2.3813 mol) of tetradecylamine was fed into a 2-l four-necked flask equipped with a stirrer, a dropping funnel and a thermometer, and heated to 90° C. Then, 208.4 g (2.421 mol) of γ-butyrolactone was dropwise added to the tetradecylamine over a period of about 0.5 hr. During this period, the temperature of the reaction system was maintained at 90° to 100° C. The obtained reaction mixture was further stirred at 100° C. for 4 hrs. The obtained crude product having a temperature of its melting point or above was dropwise added to 2.5 l of hexane to crystallize. Thus, 668.98 g of N-tetradecyl-3-hydroxybutyramide was obtained (yield: 94%). The hydroxyl value thereof was 190.7 (calculated value: 187.33). The infrared absorption spectrum data thereof were as follows:

Infrared absorption Spectrum (KBr Tablet Method)
 3300 (O—H stretching), 3100 (N—H stretching), 2920, 2855 (C—H stretching), 1642 (C=0 stretching) cm$^{-1}$ (2) Synthesis of Sodium Salt of N-tetradecyl-3-sulfoxybutyramide 401.54 g (1.3407 mol) of the N-tetradecyl-3-hydroxybutyramide obtained in the above step (1) was put in a 5-l round-bottomed flask equipped with a stirrer, a dropping funnel, a condenser tube and a thermometer. Next, 1.8 l of chloroform was put in the flask to thereby dissolve the N-tetradecyl-3-hydroxybutyramide in the chloroform. While stirring the obtained chloroform solution at room temperature under a stream of nitrogen gas, 172.5 g (1.480 mol) of chlorosulfonic acid was dropwise added thereto over a period of about 1 hr. During the period, the temperature of the reaction system was maintained at 10° to 20° C. Thereafter, the obtained mixture was further stirred at room temperature for 3 hrs. The obtained reaction mixture was poured into a mixture of 1000 g of ice water and 1 l of n-butanol. The obtained mixture was stirred for about 10 min, and transferred to a separatory funnel. An organic phase was separated. This organic phase was neutralized with a 30% aqueous NaOH solution to adjust the pH thereof to 7. Chloroform and butanol were distilled off from the organic phase under reduced pressure. The remaining solid was washed with 4 l of acetone to obtain 511.43 g of sodium salt of N-tetradecyl-3-sulfoxybutyramide (yield: 95%). The infrared absorption spectrum data, $^1$H-NMR spectrum data and mass spectrum data thereof were as follows:

Infrared Absorption Spectrum (KBr Tablet Method)
 3334 (N—H stretching), 2925, 2854 (C—H stretching), 1635 (C=0 stretching), 1206, 1070 (S=0 stretching) cm$^{-1}$ $^1$H-NMR Spectrum (δ, ppm) in D$_2$O a: 0.89 ppm (t, 3H)

b: 1.30 ppm (b, 22H)

c: 1.52 ppm (m, 2H)

d: 3.18 ppm (t, 2H)

e: 2.38 ppm (t, 2H)

f: 1.98 ppm (m, 2H)

g: 4.10 ppm (t, 2H)

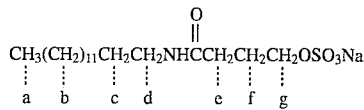

Mass Spectrum (Fab Ionization Method)
 424: (M+Na)$^+$
 322: (M+H—SO$_3$)$^+$
 282: (M—OSO$_3$Na)$^+$

EXAMPLE 8

Synthesis of Ammonium Salt of N-cocoyl-3-sulfoxybutyramide (1) Synthesis of N-cocoyl-3-hydroxybutyramide 777.36 g (3.9653 mol) of cocoyl alkylamine (Farmin CS produced by Kao Corp., having an average molecular weight of 196.04) was fed into a 2-l four-necked flask equipped with a stirrer, a dropping funnel and a thermometer, and heated to 90° C. Then, 341.39 g (3.9655 mol) of γ-butyrolactone was dropwise added to the cocoyl alkylamine over a period of about 1 hr. During this period, the temperature of the reaction system was maintained at 90° to 100° C. The obtained reaction mixture was further stirred at 100° C. for 3 hrs. The obtained crude product having a temperature of its melting point or above was dropwise added to 4 l of hexane to crystallize. Thus, 1078.4 g of N-cocoyl-3-hydroxybutyramide was obtained (yield: 96%). The hydroxyl value thereof was 202.9 (calculated value: 198.86).

(2) Synthesis of ammonium salt of N-cocoyl-3-sulfoxybutyramide 463.38 g (1.643 mol) of the N-cocoyl-3-hydroxybutyramide obtained in the above step (1) was put in a 5-l round-bottomed flask equipped with a stirrer, a dropping funnel, a condenser tube and a thermometer. Next, 2 l of chloroform was put in the flask to thereby dissolve the N-cocoyl-3-hydroxybutyramide in the chloroform. While stirring the obtained chloroform solution at room temperature under a stream of nitrogen gas, 202.0 g (1.734 mol) of chlorosulfonic acid was dropwise added thereto over a period of about 1.5 hrs. During the period, the temperature of the reaction system was maintained at 10° to 20° C. Thereafter, the obtained mixture was further stirred at room temperature for 2 hrs. The obtained reaction mixture was poured into a mixture of 1000 g of ice water and 1 l of n-butanol. The obtained mixture was stirred for about 10 min, and transferred to a separatory funnel. An organic phase was separated. This organic phase was neutralized with 25% aqueous ammonia to adjust the pH thereof to 7. Chloroform and butanol were distilled off from the organic phase under reduced pressure. The remaining solid was washed with 4 l of acetone to obtain 591.91 g of ammonium salt of N-cocoyl-3-sulfoxybutyramide (yield: 95%). The infrared absorption spectrum data thereof were as follows:

Infrared Absorption Spectrum (KBr Tablet Method)
 3260 (N—H stretching), 2926, 2855 (C—H stretching), 1634 (C=0 stretching), 1210, 1085 (S=0 stretching) cm$^{-1}$

EXAMPLE 9

Synthesis of Sodium Salt of N-dodecyl-2-methyl-4-sulfoxypentanamide 216.6 g (1.17 mol) of dodecylamine was fed into a 2-l round-bottomed flask equipped with a stirrer, a dropping funnel, a condenser tube and a thermometer, and heated to 90° C. under a stream of nitrogen gas. Then, from the dropping funnel, 133.4 g (1.17 mol) of 2-methyl-δ-valerolactone was introduced over a period of about 1 hr while stirring the dodecylamine. During this period, the temperature of the reaction mixture elevated to about 100° C. due to exothermic reaction. The obtained reaction mixture was further stirred at 100° C. for 5 hrs. Without isolating an alkanolamide, a sulfation reaction was carried out. More specifically, the reaction mixture was cooled to room temperature, and then 1000 g of methylene chloride was added to dissolve the same. At room temperature, 143.0 g (1.23 mol) of chlorosulfonic acid was dropwise added to the obtained methylene chloride solution over a period of about 1 hr. After the completion of the dropwise addition, the obtained mixture was stirred at 30° C. for about 2 hr. Then, the reaction mixture was poured into a mixture of 500 g of ice water and 500 ml of n-butanol. The obtained mixture was transferred to a separatory funnel, the funnel was vigorously shaken and then an organic phase was separated. This organic phase was neutralized with a 30% aqueous NaOH solution to adjust the pH thereof to 7.2. The solvent and water were distilled off from the organic phase under reduced pressure, and then the residue was washed with ethanol. Thus, 417.4 g of sodium salt of N-dodecyl-2-methyl-4-sulfoxypentanamide was obtained (yield: 88.7%). The infrared absorption spectrum data and $^1$H-NMR spectrum data thereof were as follows:

Infrared Absorption Spectrum (KBr Tablet Method)
 3262 (N—H stretching), 2926, 2854 (C—H stretching), 1635 (C=0 stretching), 1209, 1083 (S=0 stretching) cm$^{-1}$
$^1$H-NMR Spectrum (δ, ppm) in D$_2$O
 a, i: 0.60 ppm (m, 6H)
 b: 0.93 ppm (m, 18H)
 c: 1.33 ppm (m, 2H)
 d, f: 2.90 ppm (m, 3H)
 e: 2.03 ppm (d, 2H)
 g: 1.74 ppm (m, 2H)
 h: 3.78 ppm (t, 2H)

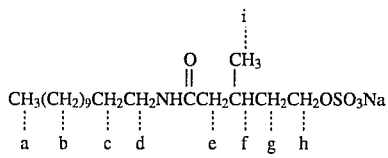

EXAMPLE 10

Synthesis of Sodium Salt of N-octyl-4-sulfoxypentanamide
(1) Synthesis of N-octyl-4-hydroxypentanamide 34.14 g (0.8641 mol) of octylamine was fed into a 100-ml four-necked flask equipped with a stirrer, a dropping funnel and a thermometer, and heated to 90° C. Then, 26.46 g (0.2643 mol) of δ-valerolactone was dropwise added to the octylamine over a period of about 10 min. During this period, the temperature of the reaction system was maintained at 90° to 100° C. The obtained reaction mixture was further stirred at 100° C. for 4 hrs. The obtained crude product having a temperature of its melting point or above was dropwise added to 400 ml of hexane to crystallize. Thus, 46.58 g of N-octyl-4-hydroxypentanamide was obtained (yield: 77%). The infrared absorption spectrum data thereof were as follows:

Infrared Absorption Spectrum (KBr Tablet Method)
 3320 (O—H stretching), 2922, 2856 (C—H stretching), 1636 (C=0 stretching) cm$^{-1}$ (2) Synthesis of Sodium Salt of N-octyl-4-sulfoxypentanamide 40.29 g (0.1757 mol) of the N-octyl-4-hydroxypentanamide obtained in the above step (1) was put in a 300-ml round-bottomed flask equipped with a stirrer, a dropping funnel, a condenser tube and a thermometer. Next, 160 ml of chloroform was put in the flask to thereby dissolve the N-octyl-4-hydroxypentanamide in the chloroform. While stirring the obtained chloroform solution at room temperature under a stream of nitrogen gas, 22.5 g (0.193 mol) of chlorosulfonic acid was dropwise added thereto over a period of about 20 min. During the period, the temperature of the reaction system was maintained at 10° to 20° C. Thereafter, the obtained mixture was further stirred at room temperature for 1 hr. The obtained reaction mixture was poured into a mixture of 150 g of ice water and 70 ml of n-butanol. The obtained mixture was stirred for about 10 min, and transferred to a separatory funnel. An organic phase was separated. Next, this organic phase was neutralized with a 30% aqueous NaOH solution to adjust the pH thereof to 7. Chloroform and butanol were distilled off from the organic phase under reduced pressure. The remaining solid was washed with 200 ml of acetone to obtain 44.84 g of sodium salt of N-octyl-4-sulfoxypentanamide (yield: 77%). The infrared absorption spectrum data, $^1$H-NMR spectrum data and mass spectrum data thereof were as follows:

Infrared Absorption Spectrum (KBr Tablet Method)
 3345 (N—H stretching), 2926, 2855 (C—H stretching), 1640 (C=0 stretching), 1200, 1077 (S=0 stretching) cm$^{-1}$
$^1$H-NMR Spectrum (δ, ppm) in D$_2$O
 a: 0.95 ppm (t, 3H)
 b: 1.28 ppm (b, 10H)
 c: 1.53 ppm (m, 2H)
 d: 3.18 ppm (t, 2H)
 e: 2.30 ppm (t, 2H)
 f: 1.75 ppm (m, 4H)
 g: 4.10 ppm (t, 2H)

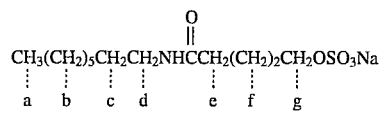

Mass Spectrum (Fab Ionization Method)
 354: (M+Na)$^+$
 252: (M+H—SO$_3$)$^+$
 212: (M—OSO$_3$Na)$^+$

EXAMPLE 11

Synthesis of Sodium Salt of N-dodecyl-4-sulfoxypentanamide (1) Synthesis of N-dodecyl-4-hydroxypentanamide 49.77 g (0.2685 mol) of dodecylamine was fed into a 100-ml four-necked flask equipped with a stirrer, a dropping funnel and a thermometer, and heated to 90° C. Then, 26.89 g (0.2686 mol) of δ-valerolactone was dropwise added to the dodecylamine over a period of about 15 min. During this period, the temperature of the reaction system was maintained at 90° to 100° C. The obtained reaction mixture was further stirred at 100° C. for 3 hrs. The obtained crude product having a temperature of its melting point or above was dropwise added to 400 ml of hexane to crystallize. Thus, 57.95 g of N-dodecyl-4-hydroxypentanamide was obtained (yield: 76%). The hydroxyl value thereof was 183.1 (calculated value: 196.54). The infrared absorption spectrum data thereof were as follows:

Infrared Absorption Spectrum (KBr Tablet Method)
 3332 (O—H stretching), 2924, 2856 (C—H stretching), 1636 (C=0 stretching) cm$^{-1}$ (2) Synthesis of Sodium Salt of N-dodecyl-4-sulfoxypentanamide 50.21 g (0.1759 mol) of the N-dodecyl-4-hydroxypentanamide obtained in the above step (1) was put in a 500-ml round-bottomed flask equipped with a stirrer, a dropping funnel, a condenser tube and a thermometer. Next, 200 ml of chloroform was put in the flask to thereby dissolve the N-dodecyl-4-hydroxypentanamide in the chloroform. While stirring the obtained chloroform solution at room temperature under a stream of nitrogen gas, 21.6 g (0.185 mol) of chlorosulfonic acid was dropwise added thereto over a period of about 20 min. During the period, the temperature of the reaction system was maintained at 10° to 20° C. Thereafter, the obtained mixture was further stirred at room temperature for 2 hrs. The obtained reaction mixture was poured into a mixture of 100 g of ice water and 100 ml of n-butanol. The obtained mixture was stirred for about 10 min, and transferred to a separatory funnel. An organic phase was separated. This organic phase was neutralized with a 30% aqueous NaOH solution to adjust the pH thereof to 7. Chloroform and butanol were distilled off from the organic phase under reduced pressure. The remaining solid was washed with 500 ml of acetone to obtain 51.57 g of sodium salt of N-dodecyl-4-sulfoxypentanamide (yield: 76%). The infrared absorption spectrum data, ¹H-NMR spectrum data and mass spectrum data thereof were as follows:

Infrared Absorption Spectrum (KBr Tablet Method)

3346 (N—H stretching), 2926, 2854 (C—H stretching), 1641 (C=0 stretching), 1197, 1077 (S=0 stretching) cm⁻¹

¹H-NMR Spectrum (δ, ppm) in D₂O a: 0.65 ppm (t, 3H)

b: 1.05 ppm (b, 18H)

c: 1.28 ppm (m, 2H)

d: 2.89 ppm (t, 2H)

e: 2.10 ppm (t, 2H)

f: 1.49 ppm (m, 4H)

g: 3.75 ppm (t, 2H)

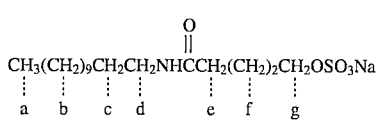

Mass Spectrum (Fab Ionization Method)

410: (M+(Na)⁺

308: (M+H—SO₃)⁺

268: (M—OSO₃Na)⁺

EXAMPLE 12

Synthesis of Sodium Salt of N-decyl-5-sulfoxyhexanamide (1) Synthesis of N-decyl-5-hydroxyhexanamide 362.56 g (2.3049 mol) of decylamine was fed into a 1-l four-necked flask equipped with a stirrer, a dropping funnel and a thermometer, and heated to 90° C. Then, 263.08 g (2.3049 mol) of ε-caprolactone was dropwise added to the decylamine over a period of about 30 min. During this period, the temperature of the reaction system was maintained at 90° to 100° C. The obtained reaction mixture was further stirred at 100° C. for 5 hrs. The obtained crude product having a temperature of its melting point or above was dropwise added to 2 l of hexane to crystallize. Thus, 528.69 g of N-decyl-5-hydroxyhexanamide was obtained (yield: 85%). The hydroxyl value thereof was 181.6 (calculated value: 206.70). The infrared absorption spectrum data thereof were as follows:

Infrared Absorption Spectrum (KBr Tablet Method)

3321 (O—H stretching), 2926, 2855 (C—H stretching), 1635 (C=0 stretching) cm⁻¹

(2) Synthesis of Sodium Salt of N-decyl-5-sulfoxyhexanamide 467.58 g (1.7226 mol) of the N-decyl-5-hydroxyhexanamide obtained in the above step (1) was put in a 5-l round-bottomed flask equipped with a stirrer, a dropping funnel, a condenser tube and a thermometer. Next, 2 l of chloroform was put in the flask to thereby dissolve the N-decyl-5-hydroxyhexanamide in the chloroform. While stirring the obtained chloroform solution at room temperature under a stream of nitrogen gas, 210.9 g (1.810 mol) of chlorosulfonic acid was dropwise added thereto over a period of about 1.5 hrs. During the period, the temperature of the reaction system was maintained at 10° to 20° C. Thereafter, the obtained mixture was further stirred at room temperature for 2 hrs. The obtained reaction mixture was poured into a mixture of 1000 g of ice water and 500 ml of n-butanol. The obtained mixture was stirred for about 10 min, and transferred to a separatory funnel. An organic phase was separated. This organic phase was neutralized with a 30% aqueous NaOH solution to adjust the pH thereof to 7. Chloroform and butanol were distilled off from the organic phase under reduced pressure. The remaining solid was washed with 4 l of acetone to obtain 521.16 g of sodium salt of N-decyl-5-sulfoxyhexanamide (yield: 81%). The infrared absorption spectrum data, ¹H-NMR spectrum data and mass spectrum data of the obtained compound were as follows:

Infrared Absorption Spectrum (KBr Tablet Method)

3316 (N—H stretching), 2926, 2854 (C—H stretching), 1635 (C=0 stretching), 1206, 1071 (S=0 stretching) cm⁻¹

¹H-NMR Spectrum (δ, ppm) in D₂O a: 0.92 ppm (t, 3H)

b: 1.38 ppm (b, 14H)

c: 1.50 ppm (m, 2H)

d: 3.19 ppm (t, 2H)

e: 2.29 ppm (t, 2H)

f: 1.71 ppm (m, 6H)

g: 4.07 ppm (t, 2H)

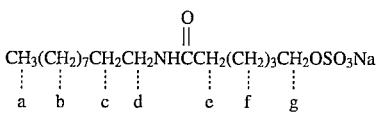

Mass Spectrum (Fab Ionization Method)

396: (M+Na)⁺

294: ( M+H—SO₃)⁺

254: (M—OSO₃Na)⁺

EXAMPLE 13

Synthesis of Sodium Salt of N-dodecyl-2-sulfoxypropionamide (1) Synthesis of N-dodecyl-2-hydroxypropionamide 25.34 g (0.1367 mol) of dodecylamine and 30 g of dioxane were fed into a 200-ml four-necked flask equipped with a stirrer, a dropping funnel and a thermometer to thereby prepare a transparent solution. Then, 9.85 g (0.1367 mol) of β-propiolactone was dropwise added to the transparent solution over a period of about 15 min. During this period, the temperature of the reaction system was maintained at 25° to 30° C. The obtained reaction mixture was further stirred at 30° C. for 5 hrs. The obtained crude product having a temperature of its melting point or above was dropwise added to 100 ml of hexane to crystallize. Thus, 28.93 g of N-dodecyl-2-hydroxypropionamide was obtained (yield: 82%). The infrared absorption spectrum data and ¹H-NMR spectrum data of the obtained compound were as follows:

Infrared Absorption Spectrum (KBr Tablet Method)

3298 (O—H stretching), 2926, 2854 (C—H stretching), 1644 (C=0 stretching) cm⁻¹

¹H-NMR Spectrum (6, ppm) in CDCl₃ a: 0.82 ppm (t, 3H)

b: 1.35 ppm (b, 18H)

c: 1.47 ppm (m, 2H)

d: 3.11 ppm (q, 2H)

e: 6.20 ppm (b, 2H)

f: 2.30 ppm (t, 2H)

g: 3.79 ppm (t, 2H)

h: 5.00 ppm (b, 1H)

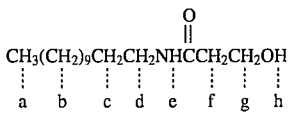

(2) Synthesis of Sodium Salt of N-dodecyl-2-sulfoxypropionamide 15.34 g (0.05959 mol) of the N-dodecyl-2-hydroxypropionamide obtained in the above step (1) was put in a 100-ml round-bottomed flask equipped with a stirrer, a dropping funnel, a condenser tube and a thermometer. Next, 100 ml of chloroform was put in the flask to thereby dissolve the N-dodecyl-2-hydroxypropionamide in the chloroform. While stirring the obtained chloroform solution at room temperature under a stream of nitrogen gas, 7.67 g (0.0658 mol) of chlorosulfonic acid was dropwise added thereto over a period of about 10 min. During the period, the temperature of the reaction system was maintained at 10° to 20° C. Thereafter, the obtained mixture was further stirred at room temperature for 1 hr. The obtained reaction mixture was poured into a mixture of 50 g of ice water and 50 ml of n-butanol. The obtained mixture was stirred for about 10 min, and transferred to a separatory funnel. An organic phase was separated. This organic phase was neutralized with a 20% aqueous NaOH solution to adjust the pH thereof to 7. Chloroform and butanol were distilled off from the organic phase under reduced pressure. The remaining solid was washed with 100 ml of acetone to obtain 19.32 g of sodium salt of N-dodecyl-2-sulfoxypropionamide (yield: 90%). The infrared absorption spectrum data, $^1$H-NMR spectrum data and mass spectrum data of the obtained compound were as follows:

Infrared Absorption Spectrum (KBr Tablet Method)

3272 (N—H stretching), 2928, 2856 (C—H stretching), 1636 (C=0 stretching), 1208, 1084 (S=0 stretching) cm$^{-1}$ $^1$H-NMR Spectrum ($\delta$, ppm) in D$_2$O a: 0.89 ppm (t, 3H)

b: 1.35 ppm (b, 18H)

c: 1.58 ppm (m, 2H)

d: 3.20 ppm (t, 2H)

e: 2.65 ppm (t, 2H)

f: 4.27 ppm (t, 2H)

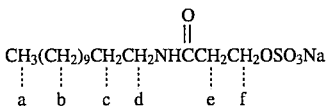

Mass Spectrum (Fab Ionization Method)

382: (M+Na)$^+$

280: (M+H—SO$_3$)$^+$

240: (M—OSO$_3$Na)$^+$

EXAMPLE 14

Synthesis of Potassium Salt of N-dodecyl-2-methyl-4-sulfoxypentanamide 150.0 g (0.81 mol) of dodecylamine was fed into a 1-l round-bottomed flask equipped with a stirrer, a dropping funnel, a condenser tube and a thermometer, and heated to 90° C. under a stream of nitrogen gas. Then, from the dropping funnel, 92.4 g (0.81 mol) of 2-methyl-δ-valerolactone was introduced over a period of about 1 hr while stirring the dodecylamine. During this period, the temperature of the reaction mixture elevated to about 100° C. due to exothermic reaction. The obtained reaction mixture was further stirred at 100° C. for 5 hrs. Without isolating an alkanolamide, a sulfation reaction was carried out. More specifically, the reaction mixture was cooled to room temperature, and 500 g of methylene chloride was added to dissolve the same. At room temperature, 99.0 g (0.85 mol) of chlorosulfonic acid was dropwise added to the obtained methylene chloride solution over a period of about 1 hr. After the completion of the dropwise addition, the obtained mixture was stirred at 30° C. for about 2 hrs. The obtained reaction mixture was poured into a mixture of 500 g of ice water and 500 ml of butanol. The obtained mixture was transferred to a separatory funnel and the funnel was vigorously shaken. An organic phase was separated. The organic phase was neutralized with a 30% aqueous KOH solution to adjust the pH thereof to 7.0. The solvent and water were distilled off from the organic phase under reduced pressure, and the residue was washed with ethanol. Thus, 308.6 g of potassium salt of N-dodecyl-2-methyl-4-sulfoxypentanamide was obtained (yield: 91.0%). The infrared absorption spectrum data and $^1$H-NMR spectrum data of the obtained compound were as follows:

Infrared Absorption Spectrum (KBr Tablet Method)

3262 (N—H stretching), 2926, 2854 (C—H stretching), 1635 (C=0 stretching), 1210, 1085 (S=0 stretching) cm$^{-1}$ $^1$H-NMR Spectrum ($\delta$, ppm) in D$_2$O a, i: 0.60 ppm (m, 6H)

b: 0.93 ppm (m, 18H)

c: 1.33 ppm (m, 2H)

d, f: 2.90 ppm (m, 3H)

e: 2.03 ppm (d, 2H)

g: 1.74 ppm (m, 2H)

h: 3.78 ppm (t, 2H)

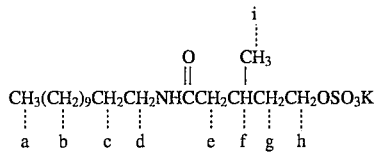

EXAMPLE 15

Synthesis of Sodium Salt of N-decylsulfoxypolyoxyethylene(EO=5)butyramide 252.8 g (1.0 mol) of the N-decyl-3-hydroxybutyramide synthesized in step (1) of Example 6 and 2 g of sodium methylate were fed into a hermetically closed reactor vessel equipped with a stirrer, a dropping funnel and a thermometer. After purging the air in the reactor vessel with nitrogen gas, the mixture in the vessel was heated to 100° C. Then, 220.0 g (5.0 mol) of ethylene oxide was introduced to the vessel at that temperature. The obtained mixture was stirred at 100° C. for 5 hrs. Next, the reaction mixture was cooled to room temperature, and 116.5 g (1.0 mol) of chlorosulfonic acid was added thereto over a period of 2 hrs. The obtained reaction mixture was further stirred at 30° C. for 1 hr, and poured into 300 g of ice water. The resultant mixture was neutralized with a 30% aqueous sodium hydroxide solution to adjust the pH thereof to 7.0. The solvent and water were distilled off from the mixture under reduced pressure, thereby obtaining 550 g of sodium salt of N-decylsulfoxypolyoxyethylene(EO=5)butyramide having 5 mol (average value) of ethylene oxide added thereto (yield: 98.6%). The sulfate purity thereof was found to be 95.5% by measurement according to the Epton method. The infrared absorption spectrum data thereof were as follows:

Infrared Absorption Spectrum (Nujol Method)

3341 (N—H stretching), 2925, 2855 (C—H stretching), 1638 (C=O stretching), 1207, 1070 (S=O stretching) cm$^{-1}$

EXAMPLE 16

Synthesis of Potassium Salt of Monolaurylglycolamide Sulfate (1) Synthesis of Monolaurylglycolamide A four-necked flask having a capacity of 1 liter and equipped with a dropping funnel, a stirrer and a thermometer was charged with 172.8 g (1.54 mol) of a 67.8% aqueous solution of glycolic acid, which was then stirred and heated in a nitrogen stream. The solution was heated up to 160° C. while effecting dehydration, and then admixed with 300.0 g (1.62 mol) of laurylamine through the dropping funnel over about 1 hour. Thereafter, the resulting mixture was stirred at 160° C. for 5 hours. The resulting reaction product was cooled to room temperature, and then dissolved in about 1.5 liters of ether. The resulting solution was transferred into a separatory funnel wherein it was then washed with 500 ml of ion-exchanged water three times. The ether phase was separated, and dried over anhydrous sodium sulfate. Ether was distilled off. The remaining solid was further dried under reduced pressure. Thus, there was obtained 348.1 g (yield: 92.9%) of monolaurylglycolamide, the hydroxyl number of which was 228.7 (theoretical value: 230.5).

On the other hand, values in the infrared absorption spectrum and $^1$H-NMR spectrum of the product were as follows.

Infrared Absorption Spectrum (KBr Tablet Method)

3334 cm$^{-1}$ (O—H stretching vibration), 3262 cm$^{-1}$ (N—H stretching vibration), 2920, 2854 cm$^{-1}$ (C—H stretching vibration), 1638 cm$^{-1}$ (C=O stretching vibration), $^1$H-NMR Spectrum (δ, ppm) in CDCl$_3$ a: 0.89 ppm (t, 3H)

b: 1.30 ppm (m, 18H)

c: 1.55 ppm (m, 2H)

d: 3.27 ppm (q, 2H)

e: 7.02 ppm (b, 1H)

f: 4.02 ppm (s, 2H)

g: 5.10 ppm (b, 1H)

$$\underset{a\ \ \ \ b\ \ \ \ c\ \ \ \ d\ \ \ \ e\ \ \ \ f\ \ \ \ g}{CH_3(CH_2)_9CH_2CH_2NH\overset{O}{\overset{\|}{C}}CH_2OH}$$

(2) Synthesis of Potassium Salt of Monolaurylglycolamide Sulfate

A four-necked flask having a capacity of 500 ml and equipped with a stirrer, a dropping funnel, a cooling tube and a thermometer was charged with 35.5 g (146 mmol) of monolaurylglycolamide synthesized in (1) above, which was then dissolved in 350 ml of chloroform. The resulting solution was stirred in a nitrogen stream at room temperature while dropwise adding thereto 17.9 g (153 mmol) of chlorosulfonic acid over about 30 minutes. In this step, the reaction system was cooled in a cool water bath in order to prevent the reaction temperature from exceeding 30° C. After the completion of the dropwise addition, the reaction system was stirred at 30° C. for 1 hour. The reaction mixture was then poured into a mixed liquid composed of 150 g of cool water and 300 ml of n-butanol. The resulting mixture was transferred into a separatory funnel wherein the organic phase was then separated. This organic phase was neutralized with a 20% aqueous solution of caustic potash. After the neutralization, the solvent was distilled off under reduced pressure, and the residue was cooled to room temperature. Precipitated crystals were collected through filtration, and then dried under reduced pressure to obtain 47.0 g (yield: 89.0%) of a white powder of potassium salt of monolaurylglycolamide sulfate. The infrared absorption spectrum and $^1$H-NMR spectrum of the product were as follows. The purity of the product as an anionic surfactant was also measured by the Epton method to be 98.0%.

Infrared Absorption Spectrum (Kbr Tablet Method)

3346 cm$^{-1}$ (N—H stretching vibration), 2926, 2854 cm$^{-1}$ (C—H stretching vibration), 1659 cm$^{-1}$ (C=O stretching vibration), 1251, 1070 cm$^{-1}$ (S=O stretching vibration), $^1$H-NMR Spectrum (δ, ppm) in CDCl$_3$ a: 0.57 ppm (t, 3H)

b: 0.97 ppm (m, 18H)

c: 1.21 ppm (m, 2H)

d: 2.90 ppm (q, 2H)

e: 7.02 ppm (b, 1H)

f: 4.15 ppm (s, 2H)

$$\underset{a\ \ \ \ b\ \ \ \ c\ \ \ \ d\ \ \ \ e\ \ \ \ f}{CH_3(CH_2)_9CH_2CH_2NH\overset{O}{\overset{\|}{C}}CH_2OSO_3K}$$

TESTING EXAMPLE 1

The foaming power of each of the salts of N-alkylcarbamylalkanol sulfate according to the present invention and comparative product listed in Table 1 was measured by the following method. The results are also shown in Table 1.

<Method for Testing Foaming Power>

To 4° DH hard water at 40° C., each of the surfactants together with lanolin was added to prepare an aqueous solution. The concentrations of the surfactant and the lanolin in the solution were 0.1% by weight and 0.3% by weight, respectively. The aqueous solution was stirred by the reversing stirring technique at 1450 rpm for 6 min. The volume of foam formed and remaining 10 sec and 120 sec after the termination of the stirring were measured.

TABLE 1

| | Surfactant | Vol. of foam (ml) | |
|---|---|---|---|
| | | after 10 sec | after 120 sec |
| Invention product | n-C$_{12}$H$_{25}$NH$\overset{O}{\overset{\|}{C}}$CH$_2$OSO$_3$Na (Ex. 1) | 190 | 168 |
| | n-C$_{12}$H$_{25}$N—$\overset{O}{\overset{\|}{C}}$CH$_2$OSO$_3$Na <br>                        CH$_3$ (Ex. 3) | 188 | 124 |

TABLE 1-continued

| Surfactant | Vol. of foam (ml) after 10 sec | after 120 sec |
|---|---|---|
| $\text{n-C}_{12}\text{H}_{25}\text{NHC(O)(CH}_2)_5\text{OSO}_3\text{Na}$ (Ex. 4) | 170 | 95 |
| $\text{n-C}_{12}\text{H}_{25}\text{NHC(O)(CH}_2)_5\text{OSO}_3\text{NH}_4$ (Ex. 5) | 185 | 125 |
| $\text{n-C}_{10}\text{H}_{21}\text{NHC(O)(CH}_2)_3\text{OSO}_3\text{Na}$ (Ex. 6) | 170 | 135 |
| $\text{n-C}_{12}\text{H}_{25}\text{NHCC(O)CH}_2\text{CH(CH}_3)(\text{CH}_2)_2\text{OSO}_3\text{Na}$ (Ex. 9) | 185 | 124 |
| $\text{n-C}_{12}\text{H}_{25}\text{NHC(O)(CH}_2)_4\text{OSO}_3\text{Na}$ (Ex. 11) | 185 | 124 |
| Comp. product $\text{C}_{12}\text{H}_{25}\text{O(CH}_2\text{CH}_2\text{O})_{3.0}\text{SO}_3\text{Na}$ | 170 | 90 |

TESTING EXAMPLE 2

With respect to each of the salts of N-alkylcarbamylalkanol sulfate according to the present invention and comparative products listed in Table 2, the irritancy to the skin was measured by the following quadruple cumulative irritation testing method. The results are also shown in Table 2.

<Quadruple Cumulative Irritation Testing Method>

An aqueous solution containing 10% by weight of each of the surfactants was applied to the healthy skin of each of five guinea pigs four times. The reaction of the skin after the fourth application of the aqueous solution was evaluated according to the following criteria. Table 2 shows the average evaluation marks.

<Evaluation Criteria>

0: no reaction was observed;
1: slight erythema was observed;
2: clear erythema was observed;
3: clear erythema accompanied by edema was observed; and
4: clear erythema accompanied by necrosis or asphyxia was observed.

TABLE 2

| | Surfactant | Average evaluation mark |
|---|---|---|
| Invention product | $\text{n-C}_{12}\text{H}_{25}\text{NHC(O)CH}_2\text{OSO}_3\text{Na}$ (Ex. 1) | 0.5 |
| | $\text{n-C}_{12}\text{H}_{25}\text{NHC(O)(CH}_2)_5\text{OSO}_3\text{NH}_4$ (Ex. 5) | 0.2 |
| | $\text{n-C}_{10}\text{H}_{21}\text{NHC(O)(CH}_2)_3\text{OSO}_3\text{Na}$ (Ex. 6) | 0.7 |
| | $\text{n-C}_{12}\text{H}_{25}\text{NHCC(O)CH}_2\text{CH(CH}_3)(\text{CH}_2)_2\text{OSO}_3\text{Na}$ (Ex. 9) | 0.8 |
| | $\text{n-C}_{12}\text{H}_{25}\text{NHC(O)(CH}_2)_4\text{OSO}_3\text{Na}$ (Ex. 11) | 0.8 |
| Comp. product | $\text{C}_{12}\text{H}_{25}\text{OSO}_3\text{Na}$ | 2.6 |
| | $\text{C}_{10}\text{H}_{21}\text{OSO}_3\text{Na}$ | 3.0 |

Hereinbelow, formulation examples of the detergent compositions of the present invention will be described.

FORMULATION EXAMPLE 1

A shampoo having the composition given below was prepared. The obtained shampoo not only was excellent in foaming power and detergency, but also ensured good feeling at the time of washing and rinsing of the hair.

| | |
|---|---|
| $\text{n-C}_{12}\text{H}_{25}\text{NHC(O)CH}_2\text{OSO}_3\text{NH}_4$ | 15% by weight |
| lauroyldiethanolamide | 3 |
| lauryldimethylamine oxide | 0.5 |
| polydimethyldiallylammonium chloride (Merquat 100 produced by CALGON) | 0.1 |
| sodium benzoate | 0.3 |
| coloring matter | appropriate amount* |
| fragrance | appropriate amount* |
| citric acid | appropriate amount* |
| water | balance to 100% |
| pH 6.5 | |

*a conventionally appropriate amount in the art (the same hereinafter).

FORMULATION EXAMPLE 2

A shampoo having the composition given below was prepared. The obtained shampoo not only was excellent in foaming power and detergency, but also ensured good feeling at the time of washing and rinsing of the hair.

| | |
|---|---|
| $\text{n-C}_{12}\text{H}_{25}\text{NHC(O)CH}_2\text{OSO}_3\text{NH}_4$ | 15% by weight |
| $\text{n-C}_{11}\text{H}_{23}\text{C(O)NH(CH}_2)_3-\text{N}^{\oplus}(\text{CH}_3)_2-\text{CH}_2\text{CO}_2^{\ominus}$ | 5 |
| lauryldimethylamine oxide | 0.5 |
| hydroxyethylcellulose (SE-850K produced by Daicel Chemical Industries, Ltd.) | 0.1 |
| sodium benzoate | 0.3 |

FORMULATION EXAMPLE 3

A shampoo having the composition given below was prepared. The obtained shampoo not only was excellent in foaming power and detergency, but also ensured good feeling without squeak at the time of washing and rinsing of the hair.

| | |
|---|---|
| $\text{n-C}_{12}\text{H}_{25}\text{NHC}(\overset{\overset{\displaystyle O}{\|\|}}{})(\text{CH}_2)_5\text{OSO}_3\text{NH}_4$ | 15% by weight |
| lauramidopropyldimethylaminoacetic acid betaine | 3 |
| cationized cellulose (Polymer JR400 produced by Union Carbide) | 0.5 |
| sodium benzoate | 0.3 |
| coloring matter | appropriate amount |
| fragrance | appropriate amount |
| citric acid | appropriate amount |
| water | balance to 100% |

FORMULATION EXAMPLE 4

A shampoo having the composition given below was prepared. The obtained shampoo not only was excellent in foaming power and detergency, but also ensured good feeling without squeak at the time of washing and rinsing of the hair.

| | |
|---|---|
| $\text{n-C}_{12}\text{H}_{25}\text{NHC}(\overset{\overset{\displaystyle O}{\|\|}}{})(\text{CH}_2)_5\text{OSO}_3\text{NH}_4$ | 17% by weight |
| polyoxyethylene(3)laurylsulfosuccinate | 3 |
| cetyltrimethylammonium chloride | 1 |
| hydroxyethylcellulose (SE-850K produced by Daicel Chemical Industries, Ltd.) | 0.1 |
| cationic starch (product of cationization of corn starch, degree of cationization: 0.3) | 0.3 |
| sodium benzoate | 0.3 |
| coloring matter | appropriate amount |
| fragrance | appropriate amount |
| citric acid | appropriate amount |
| water | balance to 100% |

FORMULATION EXAMPLE 5

A body shampoo having the composition given below was prepared. The obtained body shampoo not only was excellent in foaming power and detergency, but also ensured moist and good feeling after washing.

| | |
|---|---|
| $\text{n-C}_{12}\text{H}_{25}\text{NHCCH}_2\text{OSO}_3\text{NH}_4$ (with C=O) | 17% by weight |
| decyl polyglucoside (one represented by the above general formula (19) wherein $R^{59}$ represents a decyl group, G represents a glucose residue, x is 0 and y is 1.3) | 5 |
| lauryldimethylamine oxide | 3 |
| glycerol | 4 |
| sucrose fatty acid ester | 1 |
| methyl paraben | 0.3 |
| coloring matter | appropriate amount |
| fragrance | appropriate amount |
| citric acid | appropriate amount |
| water | balance to 100% |

FORMULATION EXAMPLE 6

A shampoo having the composition given below was prepared. The obtained shampoo not only was excellent in foaming power and detergency, but also ensured good feeling at the time of washing and rinsing of the hair.

| | |
|---|---|
| $\text{n-C}_{12}\text{H}_{25}\text{NHCCH}_2\text{CHCH}_2\text{CH}_2\text{OSO}_3\text{NH}_4$ (with C=O and CH$_3$ branch) | 15% by weight |
| lauroyldiethanolamide | 3 |
| lauryldimethylamine oxide | 0.5 |
| hydroxyethylcellulose (SE-850K produced by Daicel Chemical Industries, Ltd.) | 0.1 |
| sodium benzoate | 0.3 |
| coloring matter | appropriate amount |
| fragrance | appropriate amount |
| citric acid | appropriate amount |
| water | balance to 100% |
| pH 6.5 | |

FORMULATION EXAMPLE 7

A shampoo having the composition given below was prepared. The obtained shampoo not only was excellent in foaming power and detergency, but also ensured good feeling at the time of washing and rinsing of the hair.

| | |
|---|---|
| $\text{n-C}_{12}\text{H}_{25}\text{NHCCH}_2\text{CHCH}_2\text{CH}_2\text{OSO}_3\text{NH}_4$ (with C=O and CH$_3$ branch) | 15% by weight |
| $\text{n-C}_{11}\text{H}_{23}\text{CNH}(\text{CH}_2)_3-\overset{+}{\text{N}}(\text{CH}_3)_2-\text{CH}_2\text{CO}_2^{-}$ (with C=O) | 5 |
| lauryldimethylamine oxide | 0.5 |
| hydroxyethylcellulose (SE-850K produced by Daicel Chemical Industries, Ltd.) | 0.1 |
| sodium benzoate | 0.3 |
| coloring matter | appropriate amount |
| fragrance | appropriate amount |
| citric acid | appropriate amount |
| water | balance to 100% |
| pH 6.5 | |

FORMULATION EXAMPLE 8

A shampoo having the composition given below was prepared. The obtained shampoo not only was excellent in foaming power and detergency, but also ensured good feeling without squeak at the time of washing and rinsing of the hair.

| | |
|---|---|
| $\text{n-C}_{12}\text{H}_{25}\text{NHC}(\text{CH}_2)_3\text{OSO}_3\text{NH}_4$ (with C=O) | 15% by weight |

| | |
|---|---|
| lauramidopropyldimethylaminoacetic acid betaine | 3 |
| cationized cellulose (Polymer JR400 produced by Union Carbide) | 0.5 |
| sodium benzoate | 0.3 |
| coloring matter | appropriate amount |
| fragrance | appropriate amount |
| citric acid | appropriate amount |
| water | balance to 100% |

FORMULATION EXAMPLE 9

A shampoo having the composition given below was prepared. The obtained shampoo not only was excellent in foaming power and detergency, but also ensured good feeling without squeak at the time of washing and rinsing of the hair.

| | |
|---|---|
| $\text{n-}C_{12}H_{25}NH\overset{O}{\overset{\|}{C}}(CH_2)_3OSO_3NH_4$ | 17% by weight |
| monolauryl phosphate | 3 |
| cetyltrimethylammonium chloride | 1 |
| hydroxyethylcellulose (SE-850 produced by Daicel Chemical Industries, Ltd.) | 0.1 |
| cationized starch (product of cationization of corn starch, degree of cationization: 0.3) | 0.3 |
| sodium benzoate | 0.3 |
| coloring matter | appropriate amount |
| fragrance | appropriate amount |
| citric acid | appropriate amount |
| water | balance to 100% |

FORMULATION EXAMPLE 10

A body shampoo having the composition given below was prepared. The obtained body shampoo not only was excellent in foaming power and detergency, but also ensured moist and good feeling after washing.

| | |
|---|---|
| $\text{N-}C_{12}H_{25}NH\overset{O}{\overset{\|}{C}}CH_2\overset{CH_3}{\overset{\|}{C}H}CH_2CH_2OSO_3NH_4$ | 17% by weight |
| polyoxyethylene (3) lauryl glucoside | 5 |
| lauryldimethylamine oxide | 3 |
| glycerol | 4 |
| sucrose fatty acid ester | 1 |
| methyl paraben | 0.3 |
| coloring matter | appropriate amount |
| fragrance | appropriate amount |
| citric acid | appropriate amount |
| water | balance to 100% |

FORMULATION EXAMPLE 11

A shampoo having the composition given below was prepared. The obtained shampoo not only was excellent in foaming power and detergency, but also ensured good feeling without squeak at the time of washing and rinsing of the hair. Moreover, the shampoo exhibited excellent conditioning effect, and was especially excellent in slipperiness after drying.

| | |
|---|---|
| $\text{n-}C_{12}H_{25}NH\overset{O}{\overset{\|}{C}}CH_2OSO_3NH_4$ | 17% by weight |
| lauryl polyglucoside (one represented by the above general formula (19) wherein $R^{59}$ represents a lauryl group, G represents a glucose residue, x is 0 and y is 1.3) | 5 |
| dimethylpolysiloxane (KF-96 produced by Shin-Etsu Chemical Co., Ltd., viscosity: 200 cs) | 0.5 |
| polyoxyethylene (160 E.O.) sorbitan tristearate | 0.3 |
| sodium benzoate | 0.3 |
| coloring matter | appropriate amount |
| fragrance | appropriate amount |
| citric acid | appropriate amount |
| water | balance to 100% |

FORMULATION EXAMPLE 12

A shampoo having the composition given below was prepared. The obtained shampoo not only was excellent in foaming power and detergency, but also ensured good feeling without squeak at the time of washing and rinsing of the hair. Moreover, the shampoo exhibited excellent conditioning effect, and ensured excellent slipperiness and flexibility at the time of rinsing and after drying.

| | |
|---|---|
| $\text{n-}C_{12}H_{25}NH\overset{O}{\overset{\|}{C}}CH_2\overset{CH_3}{\overset{\|}{C}H}CH_2CH_2OSO_3Na$ | 15% by weight |
| lauryldimethylamine oxide | 3 |
| hydroxyethylcellulose (SE-850K produced by Daicel Chemical Industries, Ltd.) | 0.1 |
| cationized cellulose (Polymer JR400 produced by Union Carbide) | 0.3 |
| sodium benzoate | 0.3 |
| coloring matter | appropriate amount |
| fragrance | appropriate amount |
| citric acid | appropriate amount |
| water | balance to 100% |

FORMULATION EXAMPLE 13

A shampoo having the composition given below was prepared. The obtained shampoo not only was excellent in foaming power and detergency, but also ensured good feeling without squeak at the time of washing and rinsing of the hair. Moreover, the shampoo exhibited excellent conditioning effect, and ensured excellent slipperiness and flexibility at the time of rinsing and after drying.

| | |
|---|---|
| $\text{n-}C_{12}H_{25}NH\overset{O}{\overset{\|}{C}}CH_2OSO_3Na$ | 15% by weight |
| lauroyldiethanolamide | 2 |
| glycerol monodecanoate | 3 |
| cationized cellulose (Polymer JR400 produced by Union Carbide) | 0.3 |
| coloring matter | appropriate amount |
| fragrance | appropriate amount |
| citric acid | appropriate amount |
| water | balance to 100% |

FORMULATION EXAMPLE 14

A shampoo having the composition given below was prepared. The obtained shampoo not only was excellent in foaming power and detergency, but also ensured good feeling without squeak at the time of washing and rinsing of the hair. Moreover, the shampoo exhibited excellent conditioning effect, and ensured excellent slipperiness and flexibility at the time of rinsing and after drying.

| | |
|---|---|
| $\text{n-C}_{12}\text{H}_{25}\text{NHCCH}_2\text{OSO}_3\text{Na}$ (with C=O) | 8% by weight |
| sodium salt of polyoxyethylene (3) lauryl ether sulfate | 7 |
| lauroyldiethanolamide | 3 |
| cationized cellulose (Polymer JR400 produced by Union Carbide) | 0.3 |
| coloring matter | appropriate amount |
| fragrance | appropriate amount |
| citric acid | appropriate amount |
| water | balance to 100% |

FORMULATION EXAMPLE 15

A shampoo having the composition given below was prepared. The obtained shampoo not only was excellent in foaming power and detergency, but also ensured good feeling without squeak at the time of washing and rinsing of the hair. Moreover, the shampoo exhibited excellent conditioning effect, and ensured excellent slipperiness and flexibility at the time of rinsing and after drying.

| | |
|---|---|
| $\text{n-C}_{12}\text{H}_{25}\text{NHC(CH}_2)_3\text{OSO}_3\text{NH}_4$ (with C=O) | 10% by weight |
| polyoxyethylene (17) lauryl ether | 3 |
| laurylhydroxysulfobetaine | 3 |
| cationized polymer (Merquat 100 produced by CALGON) | 0.3 |
| coloring matter | appropriate amount |
| fragrance | appropriate amount |
| citric acid | appropriate amount |
| water | balance to 100% |

FORMULATION EXAMPLE 16

A shampoo having the composition given below was prepared. The obtained shampoo not only was excellent in foaming power and detergency, but also ensured good feeling without squeak at the time of washing and rinsing of the hair. Moreover, the shampoo exhibited excellent conditioning effect, and ensured excellent slipperiness and flexibility at the time of rinsing and after drying.

| | |
|---|---|
| $\text{n-C}_{12}\text{H}_{25}\text{NHC(CH}_2)_3\text{OSO}_3\text{NH}_4$ (with C=O) | 10% by weight |
| $\text{n-C}_{12}\text{H}_{25}\text{NHCCH}_2\text{OSO}_3\text{Na}$ (with C=O) | 5 |
| lauroylmonoethanolamide | 2 |
| cationic starch (product of cationization of corn starch, degree of cationization: 0.3) | 0.2 |
| coloring matter | appropriate amount |
| fragrance | appropriate amount |
| citric acid | appropriate amount |
| water | balance to 100% |

FORMULATION EXAMPLES 17 to 24 AND COMPARATIVE FORMULATION EXAMPLES 1 TO 3

Various detergents for tableware each having the composition specified in Table 3 were prepared, and the foaming properties thereof were evaluated according to the following method. The results are also shown in Table 3.

<Foaming Test>

To deionized water at 25° C., each of the detergents for tableware together with butter was added to prepare an aqueous solution. The concentrations of the detergent and the butter in the solution were 5% by weight and 0.2% by weight, respectively. The aqueous solution was stirred by the reversing stirring technique at 1000 rpm for 5 min. The height of the formed foam remaining in 30 sec after the termination of the stirring was measured.

TABLE 3

| | | Formulation Ex. | | | | | | | | Comp. Formulation Ex. | | |
|---|---|---|---|---|---|---|---|---|---|---|---|---|
| | | 17 | 18 | 19 | 20 | 21 | 22 | 23 | 24 | 1 | 2 | 3 |
| Detergent compn. (% by wt.) | | | | | | | | | | | | |
| $\text{C}_{12}\text{H}_{25}-\text{NH}-\text{C}(=\text{O})-\text{R}'-\text{OSO}_3\text{Na}$ | $\text{R}' = -\text{CH}_2-$ | 16 | — | 16 | 16 | — | — | — | — | — | — | — |
| | $\text{R}' = -(\text{CH}_2)_5-$ | — | 16 | — | — | — | — | — | — | — | — | — |
| | $\text{R}' = -\text{CH}_2\text{CH}_2\text{CH}_2-$ | — | — | — | — | 16 | — | 16 | 16 | — | — | — |
| | $\text{R}' = -\text{CH}_2\text{CHCH}_2\text{CH}_2-$ with $\text{CH}_3$ branch | — | — | — | — | — | 16 | — | — | — | — | — |
| $\text{C}_{12}\text{H}_{25}-\text{O}-(\text{CH}_2\text{CH}_2\text{O})_{5.0}-\text{SO}_3\text{Na}$ | | — | — | — | — | — | — | — | — | 16 | 16 | 16 |

TABLE 3-continued

|  | Formulation Ex. | | | | | | | | Comp. Formulation Ex. | | |
| --- | --- | --- | --- | --- | --- | --- | --- | --- | --- | --- | --- |
|  | 17 | 18 | 19 | 20 | 21 | 22 | 23 | 24 | 1 | 2 | 3 |
| $C_{12}H_{25}-N(CH_3)_2 \to O$ | 4 | 4 | — | — | 4 | 4 | — | — | 4 | — | — |
| $C_{11}H_{23}C(O)-NH(CH_2CH_2OH)_2$ | — | — | 4 | — | — | — | 4 | — | — | 4 | — |
| $C_{12}H_{25}-O-(CH_2CH_2O)_8H$ | — | — | — | 4 | — | — | — | 4 | — | — | 4 |
| Ethanol | 5 | 5 | 5 | 5 | 5 | 5 | 5 | 5 | 5 | 5 | 5 |
| Water | balance | balance | balance | balance | balance | balance | balance | balance | balance | balance | balance |
| Height of foam (mm) | 47 | 30 | 25 | 25 | 47 | 30 | 25 | 25 | 20 | 8 | 6 |

FORMULATION EXAMPLE 25 (A Shampoo Composition)

| | |
| --- | --- |
| $C_{12}H_{25}NHCCH_2CHC_2H_4OSO_3Na$ (with O and CH$_3$) | 15% by weight |
| lauryldimethylamineoxide | 3 |
| cationized cellulose (Polymer JR400 produced by Uhion Carbide) | 0.2 |
| polydimethylsiloxane emulsion (TSC 930 produced by Toshiba Silicone Co. Ltd.) | 5 |
| amine-modified silicone emulsion (SM 8702C produced by Toray Dow Corning Silicone Co. Ltd.) | 0.2 |
| sodium benzoate | 0.5 |
| fragrance | 0.4 |
| coloring matter | 0.0001 |
| distilled water | balance to 100% |

FORMULATION EXAMPLE 26 (A Shampoo Composition)

| | |
| --- | --- |
| $C_{12}H_{25}NHCCH_2OSO_3Na$ (O) | 10% by weight |
| alkyl polyglucoside | 10 |
| purified common salt | 2 |
| glycerol | 2 |
| polydimethylsiloxane emulsion (BY22-835 produced by Toray Dow Corning Silicone Co. Ltd.) | 4 |
| sodium benzoate | 0.5 |
| fragrance | 0.4 |
| coloring matter | 0.0001 |
| distilled water | balance to 100% |

FORMULATION EXAMPLE 27 (A Shampoo Composition)

| | |
| --- | --- |
| $C_{12}H_{25}NHCCH_2OSO_3Na$ (O) | 10% by weight |
| sodium salt of polyoxyethylene (3) lauryl ether sulfate | 10 |
| lauroyldiethanolamide | 2 |
| polydimethylsiloxane emulsion (SM 8705 produced by Toray Dow Corning Silicone Co. Ltd.) | 4 |
| sodium benzoate | 0.5 |
| fragrance | 0.4 |
| coloring matter | 0.0001 |
| distilled water | balance to 100% |

FORMULATION EXAMPLE 28 (A Shampoo Composition)

| | |
| --- | --- |
| $C_{12}H_{25}NHCC_5H_{10}OSO_3Na$ (O) | 14% by weight |
| alkyl polyglucoside | 5 |
| glycerol monodecanoate | 2 |
| propylene glycol | 3 |
| polyether-modified silicone (Silicone KF-6005 produced by Shin-Etsu Chemical Industries Co. Ltd.) | 0.3 |
| polydimethylsiloxane emulsion (XS65-A2773 produced by Toshiba Silicone Co. Ltd.) | 3 |
| sodium benzoate | 0.5 |
| fragrance | 0.4 |
| coloring matter | 0.0001 |
| distilled water | balance to 100% |

EXAMPLE 16 AND COMPARATIVE EXAMPLES 1 TO 3

Lustrous shampoo compositions having respective recipes as shown in Table 4 were prepared, and evaluation test thereon were carried out according to the following methods. The results are shown in Table 4.

<Evaluation Test Methods>

20 women were panelists. 20 g of a hair bundle (15 cm) of each panelist was coated with 1 g of each shampoo composition having a recipe as shown in Table 4, then washed, rinsed with running water of 40° C., and dried with a dryer to evaluate the easiness of foaming during hair washing, the state of foaming during hair washing, the slipperiness and passability between fingers of hair during hair washing, rinsing and drying, and the starchy feeling of hair during drying according to the following ratings.

Ratings

Easiness of foaming during hair washing
⊚: Very easy to foam, o: slightly easy to foam,
Δ: slightly hard to foam, x: hard to foam.
State of foaming during hair washing
⊚: very much foamed, o: slightly much,
Δ: a little, x: insufficient.
Slipperiness and passability between fingers during hair washing, rinsing and drying
⊚: slippery, o: slightly slippery,
Δ: slightly squeaky, x: considerably squeaky.
Starchy feeling during hair drying
o: not starchy, Δ: slightly starchy,
x: considerably starchy.

TABLE 4

|  |  | Comp. Ex. 1 | Comp. Ex. 2 | Comp. Ex. 3 | Ex. 1 |
|---|---|---|---|---|---|
| Shampoo Recipe (%) | sodium salt of polyoxyethylene(3) laurylsulfate | 20.0 | — | 10.0 | 10.0 |
|  | potassium salt of monolaurylglycolamidesulfate | — | — | — | 10.0 |
|  | sodium monolaurylphosphate | — | 15.0 | 10.0 | — |
|  | distearyl ethylene glycol | 0.3 | — | 0.3 | — |
|  | sodium chloride | — | 8.0 | — | — |
|  | potassium chloride | — | — | — | 1.0 |
| Results of Evaluation Tests | During Hair Washing — Easiness of Foaming | o | ⊚ | o | ⊚ |
|  | During Hair Washing — State of Foaming | o | ⊚ | o | ⊚ |
|  | During Hair Washing — Slipperiness/Passability between Fingers | o | o | o | ⊚ |
|  | During Rinsing — Slipperiness/Passability between Fingers | Δ | x | x | o |
|  | During Drying — Slipperiness/Passability between Fingers | Δ | x | x | o |
|  | During Drying — Starchy Feeling | Δ | x | x | o |

FORMULATION EXAMPLE 29

A shampoo having the following recipe was prepared. The shampoo obtained had a pearly appearance at room temperature, excellent foaming properties and an excellent detergency, and involved no squeaky feeling during rinsing and no starchy feeling during drying.

| sodium polyoxyethylene(3) laurylsulfate | 15.0% by weight |
|---|---|
| potassium salt of monolaurylglycolamide sulfate | 15.0 |
| lauroyldiethanolamide | 2.5 |
| potassium chloride | 1.5 |
| propylene glycol | 2.0 |
| citric acid | 3.0 |
| coloring matter | suitable amount |
| perfume | suitable amount |
| preservative | suitable amount |
| purified water | q.s. ad 100% by weight |

FORMULATION EXAMPLE 30

A shampoo having the following recipe was prepared. The shampoo obtained had a pearly appearance at room temperature, excellent foaming properties and an excellent detergency, involved no squeaky feeling during rinsing, and provided excellent slipperiness and passability between fingers of hair during drying.

| sodium monoethanollaurylamide polyoxyethylene(2) ether acetate | 12.0 wt. % |
|---|---|

$$C_{11}H_{23}-\overset{\overset{O}{\|}}{C}-N\overset{H}{\underset{(CH_2CH_2O)_3CH_2COONa}{\diagdown}}$$

| potassium salt of monolaurylglycolamide sulfate | 12.0 |
|---|---|
| betaine laurylamidopropyldimethylaminoacetate | 3.0 |
| cationized cellulose*¹ | 0.3 |
| dimethylpolysiloxane emulsion*² | 3.5 |
| potassium chloride | 1.5 |
| propylene glycol | 2.0 |
| stearyltrimethylammonium chloride | 1.0 |
| citric acid | suitable amount |
| coloring matter | suitable amount |
| perfume | suitable amount |
| preservative | suitable amount |
| purified water | q.s. ad 100% by weight |

Note)
*¹Polymer JR400 manufactured by Union Carbide Japan K. K.
*²BY22-835 manufactured by Dow Corning Toray Silicone Co., Ltd.

FORMULATION EXAMPLE 31

A shampoo having the following recipe was prepared. The shampoo obtained had a pearly appearance at room temperature, excellent foaming properties and an excellent detergency, and involved no squeaky feeling during rinsing and no starchy feeling during drying.

| sodium polyoxyethylene(3) laurylsulfate | 12.0% by weight |
|---|---|

-continued

| potassium salt of monolauryl-glycolamide sulfate | 10.0 |
| sodium salt of monolauryl-glycolamide sulfate | 2.0 |
| propylene glycol | 2.0 |
| hydroxyethylcellulose*¹ | 0.1 |
| silicone emulsion*² | 1.0 |
| (myristoyl-N-hydroxyethyl)-aminoethyl-2-hydroxypropyl-trimethylammonium chloride | 2.0 |
| citric acid | suitable amount |
| coloring matter | suitable amount |
| preservative | suitable amount |
| purified water | suitable amount |
| total: | 100% by weight |

Note)
*¹HEC-SE850 manufactured by Shin-Etsu Chemical Co., Ltd.
*²SM-8702C manufactured by Dow Corning Toray Silicone Co., Ltd.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claim is:

1. An N-alkylcarbamylalkanol sulfate or a salt thereof represented by the general formulae (1-1) or (1-2):

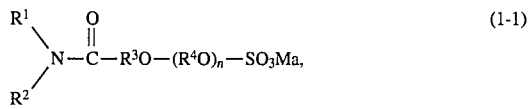

and

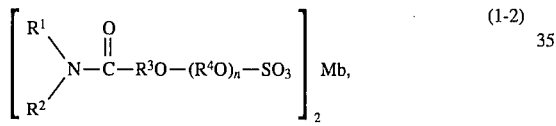

wherein $R^1$ represents a linear alkyl or alkenyl group having 6 to 22 carbon atoms; $R^2$ represents a hydrogen atom or a methyl group; $R^3$ represents a linear or branched alkylene group having 1 to 5 carbon atoms; $R^4O$ represents an oxyalkylene group having 2 or 3 carbon atoms; n represents an average addition mole number of the oxyalkylene group and is a number between 0 and 20, and wherein each $R^4O$ group may be the same or different from one another; Ma represents a hydrogen atom, an alkali metal atom, an ammonium group, an alkanol-ammonium group having 2 to 9 carbon atoms in total, an alkylammonium group having 1 to 22 carbon atoms in total, an alkenylammonium group having 2 to 22 carbon atoms in total, a $C_1$–$C_{18}$ alkyl- or $C_2$–$C_{18}$ alkenyl-substituted pyridinium group, or a group consisting of a basic amino acid and a hydrogen atom; and Mb represents an alkaline earth metal atom.

2. The N-alkylcarbamylalkanol sulfate or the salt thereof according to claim 1, which is represented by the general formula (1-1) wherein $R^1$ represents a linear alkyl group having 6 to 22 carbon atoms; $R^2$ represents a hydrogen atom or a methyl group; $R^3$ represents a linear or branched alkylene group having 1 to 5 carbon atoms; $R^4O$ represents an oxyethylene group or an oxypropylene group; n is a number between 0 and 10; and Ma represents an ammonium group, sodium, potassium or an alkanolammonium having 2 to 9 carbon atoms in total.

3. The N-alkylcarbamylalkanol sulfate or the salt thereof according to claim 2, which is represented by the general formula (1-1) wherein $R^2$ represents a hydrogen atom; $R^3$ represents a linear or branched alkylene group having 2 to 5 carbon atoms.

4. The N-alkylcarbamylalkanol sulfate or the salt thereof according to claim 1, which is represented by the general formula (1-1) wherein $R^1$ represents a linear alkyl group having 8 to 18 carbon atoms; $R^2$ represents a hydrogen atom or a methyl group; $R^3$ represents a linear alkylene group having 1 to 5 carbon atoms; n is 0; and Ma represents an ammonium group, sodium or a triethanolammonium group.

5. The N-alkylcarbamylalkanol sulfate or the salt thereof according to claim 1, which is represented by the general formula (1-1) wherein $R^1$ represents a linear alkyl group having 8 to 18 carbon atoms; $R^2$ represents a hydrogen atom; $R^3$ represents a linear or branched alkylene group having 3 to 5 carbon atoms; n is 0; and Ma represents an ammonium group, sodium or a triethanolammonium group.

6. The N-alkylcarbamylalkanol sulfate or the salt thereof according to claim 1, which is represented by the general formula (1-1) wherein $R^1$ represents a linear alkyl group having 8 to 18 carbon atoms; $R^2$ represents a hydrogen atom; $R^3$ represents a methylene group, a pentamethylene group or a 2-methylbutylene group; n is 0; and Ma represents an ammonium group, sodium or a triethanolammonium group.

7. The N-alkylcarbamylalkanol sulfate or the salt thereof according to claim 6, which is represented by the general formula (1-1) wherein $R^3$ represents a 2-methylbutylene group.

8. The N-alkylcarbamylalkanol sulfate or the salt thereof according to claim 6, which is represented by the general formula (1-1) wherein $R^3$ represents a methylene group.

9. The N-alkylcarbamylalkanol sulfate or a salt thereof according to claim 1, having the following formula:

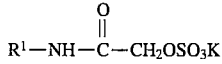

wherein $R^1$ stands for a linear alkyl or alkenyl group having 8 to 18 carbon atoms.

10. A detergent composition comprising an amount effective to provide detergency of one or more N-alkyl-carbamylalkanol sulfates or salts thereof according to claim 1; and conventional detergent ingredients.

11. The detergent composition according to claim 10, wherein in said N-alkyl-carbamylalkanol sulfate of (1-1) or (1-2) n=0.

12. The detergent composition according to claim 10, wherein said amount of N-alkylcarbamylalkanol sulfate or the salt thereof is 1 to 70% by weight based on the entire weight of the detergent composition.

13. The detergent composition according to claim 10, which further comprises at least one component selected from the group consisting of a silicone derivative, a cationic surfactant, a water-soluble cationic polymer, an anionic surfactant, a nonionic surfactant, an amphoteric surfactant, a humectant, a bactericide, an emulsifier, a fragrance, a coloring matter and water.

14. A detergent composition comprising an amount effective to provide detegency of an N-alkylcarbamylalkanol sulfate represented by the formula:

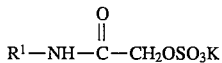

wherein $R^1$ stands for a linear alkyl or alkenyl group having 8 to 18 carbon atoms;
and conventional detergent ingredients.

15. The composition as claimed in claim 14, wherein $R^1$ is a linear alkyl or alkenyl group having 10 to 14 carbon atoms.

16. The composition as claimed in claim 14, wherein $R^1$ is a dodecyl group.

17. The composition as claimed in any one of claims 14, 15 or 16, which further comprises an N-alkylcarbamylalkanol sulfate represented by the formula (1-4):

$$R^1-NH-\overset{\overset{O}{\|}}{C}-CH_2OSO_3M \qquad (1-4)$$

wherein $R^1$ stands for a linear or branched alkyl or alkenyl group having 8 to 18 carbon atoms; and M stands for an alkali metal except for potassium, an alkaline earth metal, ammonium, an alkanolammonium, an alkylammonium, an alkenylammonium, an alkyl- or alkenyl-substituted pyridinium, or a basic amino acid.

18. The composition as claimed in claim 17, wherein M of formula (1-4) is sodium, ammonium or triethanolammonium.

19. A method for cleansing the skin or hair which comprises applying to the skin or hair a composition according to claim 10, 14, or 16.

20. A method for manifesting a pearly luster to a detergent composition which comprises adding the compound as defined in claim 14 to said detergent composition.

* * * * *